(12) United States Patent
Itoh et al.

(10) Patent No.: US 7,259,248 B2
(45) Date of Patent: Aug. 21, 2007

(54) HUMAN FGF-21 POLYPEPTIDES

(75) Inventors: Nobuyuki Itoh, Kyoto (JP); W Michael Kavanaugh, Mill Valley, CA (US)

(73) Assignees: Chiron Corporation, Emeryville, CA (US); Kyoto University, Kyoto (JP)

( * ) Notice: Subject to any disclaimer, the term of this patent is extended or adjusted under 35 U.S.C. 154(b) by 629 days.

(21) Appl. No.: 10/060,765

(22) Filed: Jan. 29, 2002

(65) Prior Publication Data

US 2002/0164713 A1 Nov. 7, 2002

Related U.S. Application Data

(62) Division of application No. 09/715,805, filed on Nov. 16, 2000, now Pat. No. 6,716,626.

(60) Provisional application No. 60/203,633, filed on May 11, 2000, provisional application No. 60/166,540, filed on Nov. 18, 1999.

(51) Int. Cl.
*C07K 14/50* (2006.01)
*C07K 7/00* (2006.01)

(52) U.S. Cl. ...................... 530/399; 530/300

(58) Field of Classification Search ............. 530/350, 530/300; 514/12
See application file for complete search history.

(56) References Cited

U.S. PATENT DOCUMENTS

| | | | | |
|---|---|---|---|---|
| 5,766,883 | A | 6/1998 | Ballance et al. | 435/69.7 |
| 5,876,969 | A | 3/1999 | Fleer et al. | 435/69.7 |
| 6,639,063 | B1 * | 10/2003 | Edwards et al. | 536/23.5 |
| 2001/0012628 | A1 * | 8/2001 | Agarwal et al. | 435/69.1 |

FOREIGN PATENT DOCUMENTS

| WO | WO97/24445 | 7/1997 |
|---|---|---|
| WO | WO97/25345 | 7/1997 |
| WO | WO99/27100 | 6/1999 |
| WO | WO 00/54813 | 9/2000 |
| WO | WO 00/60085 | 10/2000 |
| WO | WO 01/07595 | 2/2001 |
| WO | WO 01/18209 | 3/2001 |
| WO | WO 01/18210 | 3/2001 |

OTHER PUBLICATIONS

Smallwood et al., Fibroblast growth factor (FGF) homologous factors: new members of the FGF family implicated in nervous system development. Proc. Natl. Acad. Sci. USA 93:9850-9857, 1996.*
Baird and Klagsbrun, "The Fibroblast Growth Factor Family," *Cancer Cells* 3(6): 239-243, Jun. 1991.
Belluardo et al., "Comparative Localization of Fibroblast Growth Factor Receptor-1, -2, and -3 mRNAs in the Rat Brain: In Situ Hybridization Analysis," *The Journal of Comparative Neurology* 379: 226-246, 1997.
Burgess and Maciag, "The Heparin-Binding (Fibroblast) Growth Factor Family of Proteins," *Annu. Rev.Biochem.58*: 575-606, 1989.
Coulier et al., "The *FGF6* Gene within the *FGF* Multigene Family," *Annals of the New York Academy of Sciences 638*:53-61, 1991.
Crossley and Martin, "The mouse *Fgf8* gene encodes a family of polypeptides and is expressed in regions that direct outgrowth and patterning in the developing embryo," *Development 121*: 439-451, 1995.
Genbank Accession No. AB006136, Jul. 20, 2000.
Genbank Accession No. AV050323, Jun. 22, 1999.
Dickson et al., "Expression, Processing, and Properties of int-2," *Annals of the New York Academy of Sciences 638*: 18-26, 1991.
Gemel et al., "Structure and Sequence of Human *FGF8,*" *Genomics 35*: 253-257, 1996.
Ghosh et al., "Molecular Cloning and Characterization of Human *FGF8* Alternative Messenger RNA Forms," *Cell Growth & Differentiation 7*: 1425-1434, Oct. 1996.
Goldfarb et al., "Expression and Possible Functions of the FGF-5 Gene," *Annals of the New York Academy of Sciences 638*: 38-52, 1991.
Gospodarowicz and Cheng, "Heparin Protects Basic and Acidic FGF From Inactivation," *Journal of Cellular Physiology 128*: 475-484, 1986.
Hoshikawa et al., "Structure and Expression of a Novel Fibroblast Growth Factor, FGF-17, Preferentially Expressed in the Embryonic Brain," *Biochemical and Biophysical Research Communications 244*: 187-191, 1998.
Lopez et al., "Basic Fibroblast Growth Factor in a Porcine Model of Chronic Myocardial Ischemia: A Comparison of Angiographic, Echocardiographic and Coronary Flow Parameters," *The Journal of Pharmacology and Experimental Therapeutics 282*(1): 385-390, 1997.
McWhirter et al., "A novel fibroblast growth factor gene expressed in the developing nervous system is a downstream target of the chimeric homeodomain oncoprotein E2A-Pbx1," *Development 124*: 3221-3232, 1997.
Miyake et al., "Structure and Expression of a Novel Member, FGF-16, of the Fibroblast Growth Factor Family," *Biochemical and Biophysical Research Communications 243*: 148-152, 1998.
Nishimura et al., "Identification of a Novel FGF, FGF-21, Preferentially Expressed in the Liver," *Biochim. Biophys. Acta 1492*(1):203-206, Jun. 21, 2000.
Nishimura et al., "Structure and expression of a novel human FGF, FGF-19, expressed in the fetal brain," *Biochimica et Biophysica Acta 1444*: 148-151, 1999.

(Continued)

*Primary Examiner*—Ruixiang Li
(74) *Attorney, Agent, or Firm*—Jane E. R. Potter; Lisa E. Alexander; Alisa A. Harbin

(57) ABSTRACT

This invention relates to human fibroblast growth factor (hFGF-21), and to variants thereof and to polynucleotides encoding FGF-21. The invention also relates to diagnostic and therapeutic agents related to the polynucleotides and proteins, including probes and antibodies, and to methods of treating liver disease such as cirrhosis and cancer, methods of treating conditions related to thymic function, and methods of treating conditions of the testis. The invention also relates to mouse fibroblast growth factor (mFGF-21), and to variants thereof and polynucleotides encoding mFGF-21.

3 Claims, 14 Drawing Sheets

OTHER PUBLICATIONS

Ohbayashi et al., "Structure and Expression of the mRNA Encoding a Novel Fibroblast Growth Factor, FGF-18," *The Journal of Biological Chemistry* 273(29): 18161-18164, Jul. 7, 1998.

Ohuchi et al., "The mesenchymal factor, FGF10, initiates and maintains the outgrowth of the chick limb bud through interaction with FGF8, an apical ectodermal factor," *Development* 124: 2235-2244, 1997.

Ozawa et al., "Expression of the fibroblast growth factor family and their receptor family genes during mouse brain development," *Molecular Brain Research* 41: 279-288, 1996.

Reich-Slotkey et al., "Chimeric Molecules between Keratinocyte Growth Factor and Basic Fibroblast Growth Factor Define Domains That Confer Receptor Binding Specificities," *The Journal of Biological Chemistry* 270(50): 29813-29818, Dec. 15, 1995.

Smallwood et al., "Fibroblast growth factor (FGF) homologous factors: New members of the FGF family implicated in nervous system development," *Proceedings of the National Academy of Science USA* 93: 9850-9857, Sep. 1996.

Tanaka et al., "Cloning and characterization of an androgen-induced growth factor essential for the androgen-dependent growth of mouse mammary carcinoma cells," *Proceedings of the National Academy of Science USA* 89: 8928-8932, Oct. 1992.

Tanaka et al., "Human androgen-induced growth factor in prostate and breast cancer cells: its molecular cloning and growth properties," *FEBS Letters* 363: 226-230, 1995.

Wilke et al., "Expression of Fibroblast Growth Factor Receptors (FGFR1, FGFR2, FGFR3) in the Developing Head and Face," *Developmental Dynamics* 210: 41-52, 1997.

Yamasaki et al., "Structure and Expression of the Rat mRNA Encoding a Novel Member of the Fibroblast Growth Factor Family," *The Journal of Biological Chemistry* 271(27): 15918-15921, Jul. 5, 1996.

Yoshida et al., "Characterization of the *hst-1* Gene and Its Product," *Annals of the New York Academy of Sciences* 638: 27-37, 1991.

* cited by examiner

```
human FGF-21    MDSDETGFEHSGLWVSVLAGLLLGACQAHPIPDSSPLLQFG-GQV-RQRYLYTD     52
                 ** *  *  *  *   *    * **  * *    *  ***
mouse FGF-15  MARKWNGRAVARALVLATLWLAVS-GRPLAQ-QSQSVSDEDPLFLYGWGKITRLQYLYSA  58

DAQQTEAHLEIREDGTVGGAADQSPESLLQLKALKPGVIQILGVKTSRFLCQRPDGALYG  112
                * ** ** *      **     **    *    * *  *   * **   ** **
              GPYVSNCFLRIRSDGSVDCEEDQNERNLLEFRAVALKTIAIKDVSSVRYLCMSADGKIYG  118

SLHFDPEACSFRELLLEDGYNVYQSEAHGLPLHLPGNKSPHRDPAPRGPARFLPLPGLPP  172
               * * ***    *** * * **          * *          * * *
              LIRYSEEDCTFREEMDCLGYNQYRSMKHHLHIIFIQAK-PREQLQDQKPSNFIPVFHRSF  177

ALPEPPGILAPQ--PPDVGSSDPLSMVGPSQG--RSPSYAS
                *    * **  **          ***
              FETGDQLRSKMFSLPLESDSMDPFRMVEDVDHLVKSPSFQK
```

*Fig. 1*

Human FGF-21    MDSDETGFEHSGLWVSVLAGLLLG-ACQAHPIPDSSPLLQF--GGQVRQRYLYTDDAQQ-   56
                   *  **** *  *         *  *       *  * ***
Human FGF-19    MRSGCVVVHVW--ILAGLWLAVAGRPLAFSDAGPHVHYGWGDPIRLRHLYTSGPHGL    55

TEAHLEIREDGTVGGAADQSPESLLQLKALKPGVIQILGVKTSRFLCQRPDGALYGSLHF  116
                 *   *  *  * **    * **   *        * *
                SSCFLRIRADGVVDCARGQSAHSLLEIKAVALRTVAIKGVHSVRYLCMGADGKMQGLLQY  115

DPEACSFRELLLEDGYNVYQSEAHGLPLHLPGNKSPH--RDPAPRGPARFLPLPGLPPAL  174
                 * * *  ****  ** *   *              ***         *
                SEEDCAFEEEIRPDGYNVYRSEKHRLPVSLSSAKQRQLYKNRGFLPLSHFLPMLPMVPEE  175

PEP-PGILAPQ----PPDVGSSDPLSMV-GPSQGRSPSYAS   209
                **   * *       *  * **  * *     ****
                PEDLRGHLESDMFSSPLETDSMDPFGLVTGLEAVRSPSFEK   216

*Fig. 2*

Filename: mouse FGF-21 cDNA in pGEM-T
Sequence Size: 659
Sequence Position: 1 - 659
Translation Position: 14 - 646

```
              10        20        30        40        50        60
     GAGCGCAGCCCTGATGGAATGGATGAGATCTAGAGTTGGGACCCTGGGACTGTGGGTCCG     SEQ ID NO:1
                   M  E  W  M  R  S  R  V  G  T  L  G  L  W  V  R     SEQ ID NO:2

70        80        90       100       110       120
     ACTGCTGCTGGCTGTCTTCCTGCTGGGGGTCTACCAAGCATACCCCATCCCTGACTCCAG
      L  L  L  A  V  F  L  L  G  V  Y  Q  A  Y  P  I  P  D  S  S 130       140       150       160       170       180
     CCCCCTCCTCCAGTTTGGGGGTCAAGTCCGGCAGAGGTACCTCTACACAGATGACGACCA
      P  L  L  Q  F  G  G  Q  V  R  Q  R  Y  L  Y  T  D  D  D  Q 190       200       210       220       230       240
     AGACACTGAAGCCCACCTGGAGATCAGGGAGGATGGAACAGTGGTAGGCGCAGCACACCG
      D  T  E  A  H  L  E  I  R  E  D  G  T  V  V  G  A  A  H  R 250       260       270       280       290       300
     CAGTCCAGAAAGTCTCCTGGAGCTCAAAGCCTTGAAGCCAGGGGTCATTCAAATCCTGGG
      S  P  E  S  L  L  E  L  K  A  L  K  P  G  V  I  Q  I  L  G 310       320       330       340       350       360
     TGTCAAAGCCTCTAGGTTTCTTTGCCAACAGCCAGATGGAGCTCTCTATGGATCGCCTCA
      V  K  A  S  R  F  L  C  Q  Q  P  D  G  A  L  Y  G  S  P  H 370       380       390       400       410       420
     CTTTGATCCTGAGGCCTGCAGCTTCAGAGAACTGCTGCTGGAGGACGGTTACAATGTGTA
      F  D  P  E  A  C  S  F  R  E  L  L  L  E  D  G  Y  N  V  Y 430       440       450       460       470       480
     CCAGTCTGAAGCCCATGGCCTGCCCCTGCGTCTGCCTCAGAAGGACTCCCCAAACCAGGA
      Q  S  E  A  H  G  L  P  L  R  L  P  Q  K  D  S  P  N  Q  D 490       500       510       520       530       540
     TGCAACATCCTGGGGACCTGTGCGCTTCCTGCCCATGCCAGGCCTGCTCCACGAGCCCCA
      A  T  S  W  G  P  V  R  F  L  P  M  P  G  L  L  H  E  P  Q
```

*Fig. 4A*

```
            550       560       570       580       590       600
AGACCAAGCAGGATTCCTGCCCCCAGAGCCCCCAGATGTGGGCTCCTCTGACCCCCTGAG
 D   Q   A   G   F   L   P   P   E   P   P   D   V   G   S   S   D   P   L   S 610       620       630       640       650       660
CATGGTAGAGCCTTTACAGGGCCGAAGCCCCAGCTATGCGTCCTGACTCTTCCTGAATC
 M   V   E   P   L   Q   G   R   S   P   S   Y   A   S   *
```

*Fig. 4B*

Filename: human FGF-21 cDNA in pGEM-T
Sequence Size: 643
Sequence Position: 1 - 643
Translation Position: 9 - 638;

```
           10        20        30        40        50        60
agccattgatggactcggacgagaccggggttcgagcactcaggactgtgggtttctgtgc   SEQ ID NO:3
         M  D  S  D  E  T  G  F  E  H  S  G  L  W  V  S  V  L   SEQ ID NO:4

70        80        90       100       110       120
tggctggtcttctgctgggagcctgccaggcacaccccatccctgactccagtcctctcc
 A  G  L  L  L  G  A  C  Q  A  H  P  I  P  D  S  S  P  L  L 130       140       150       160       170       180
tgcaattcggggggccaagtccggcagcggtacctctacacagatgatgcccagcagacag
 C  N  S  G  G  P  S  P  A  A  V  P  L  H  R  *  *  *  *  *
```

(Note: amino acids shown in image as: Q F G G Q V R Q R Y L Y T D D A Q Q T E)

```
          190       200       210       220       230       240
aagcccacctggagatcagggaggatgggacggtggggggcgctgctgaccagagccccg
 A  H  L  E  I  R  E  D  G  T  V  G  G  A  A  D  Q  S  P  E 250       260       270       280       290       300
aaagtctcctgcagctgaaagccttgaagccgggagttattcaaatcttgggagtcaaga
 S  L  L  Q  L  K  A  L  K  P  G  V  I  Q  I  L  G  V  K  T 310       320       330       340       350       360
catccaggttcctgtgccagcggccagatggggccctgtatggatcgctccactttgacc
 S  R  F  L  C  Q  R  P  D  G  A  L  Y  G  S  L  H  F  D  P 370       380       390       400       410       420
ctgaggcctgcagcttccgggagctgcttcttgaggacggatacaatgtttaccagtccg
 E  A  C  S  F  R  E  L  L  L  E  D  G  Y  N  V  Y  Q  S  E 430       440       450       460       470       480
aagcccacggcctcccgctgcacctgccagggaacaagtccccacaccgggaccctgcac
 A  H  G  L  P  L  H  L  P  G  N  K  S  P  H  R  D  P  A  P 490       500       510       520       530       540
cccgaggaccagctcgcttcctgccactaccaggcctgccccccgcactcccggagccac
 R  G  P  A  R  F  L  P  L  P  G  L  P  P  A  L  P  E  P  P
```

*Fig. 5A*

```
        550       560       570       580       590       600
ccggaatcctggccccccagccccccgatgtgggctcctcggaccctctgagcatggtgg
  G  I  L  A  P  Q  P  P  D  V  G  S  S  D  P  L  S  M  V  G 610       620       630       640       650
gaccttcccagggccgaagccccagctacgcttcctgaagcca
  P  S  Q  G  R  S  P  S  Y  A  S  *
```

*Fig. 5B* human FGF-21   MDSDETGFEHSGLWVS-VLAGLLLGACQAHPIPDSSPLLQFGGQVRQRYLYTDDAQQTEA   59
              *    **    *   *********************  * ***
mouse FGF-21   MEWMRSRVGTLGLWVRLLLAVFLLGVYQAYPIPDSSPLLQFGGQVRQRYLYTDDDQDTEA   60

HLEIREDGTVGGAADQSPESLLQLKALKPGVIQILGVKTSRFLCQRPDGALYGSLHFDPE   119
              ********  *   ****  ************  *  ***  ***
              HLEIREDGTVVGAAHRSPESLLELKALKPGVIQILGVKASRFLCQQPDGALYGSPHFDPE   120

ACSFRELLLEDGYNVYQSEAHGLPLHLPGNKSPHRDPAPRGPARFLPLPGLPPALPEPPG   179
              **********************      **   *      *              *
              ACSFRELLLEDGYNVYQSEAHGLPLRLPQKDSPNQDATSWGPVRFLPMPGLLHEPQDQAG   180

ILAPQPPDVGSSDPLSMVGPSQGRSPSYAS   209
              *  *  *************  *  *********
              FLPPEPPDVGSSDPLSMVEPLQGRSPSYAS   210

*Fig. 6*

Codon usage for yeast (highly expressed) genes

| AmAcid | Codon | Number | /1000 | Fraction |
|---|---|---|---|---|
| Gly | GGG | 33.00 | 0.86 | 0.01 |
| Gly | GGA | 70.00 | 1.82 | 0.02 |
| Gly | GGT | 2672.00 | 69.62 | 0.91 |
| Gly | GGC | 171.00 | 4.46 | 0.06 |
| Glu | GAG | 277.00 | 7.22 | 0.10 |
| Glu | GAA | 2442.00 | 63.63 | 0.90 |
| Asp | GAT | 1100.00 | 28.66 | 0.48 |
| Asp | GAC | 1211.00 | 31.55 | 0.52 |
| Val | GTG | 117.00 | 3.05 | 0.04 |
| Val | GTA | 75.00 | 1.95 | 0.03 |
| Val | GTT | 1548.00 | 40.33 | 0.56 |
| Val | GTC | 1026.00 | 26.73 | 0.37 |
| Ala | GCG | 36.00 | 0.94 | 0.01 |
| Ala | GCA | 203.00 | 5.29 | 0.06 |
| Ala | GCT | 2221.00 | 57.87 | 0.65 |
| Ala | GCC | 969.00 | 25.25 | 0.28 |
| Arg | AGG | 20.00 | 0.52 | 0.01 |
| Arg | AGA | 1336.00 | 34.81 | 0.83 |
| Ser | AGT | 116.00 | 3.02 | 0.05 |
| Ser | AGC | 94.00 | 2.45 | 0.04 |
| Lys | AAG | 2365.00 | 61.62 | 0.78 |
| Lys | AAA | 651.00 | 16.96 | 0.22 |
| Asn | AAT | 347.00 | 9.04 | 0.22 |
| Asn | AAC | 1259.00 | 32.80 | 0.78 |
| Met | ATG | 766.00 | 19.96 | 1.00 |
| Ile | ATA | 43.00 | 1.12 | 0.02 |
| Ile | ATT | 1223.00 | 31.87 | 0.52 |
| Ile | ATC | 1070.00 | 27.88 | 0.46 |
| Thr | ACG | 28.00 | 0.73 | 0.01 |

*Fig. 7A*

| | | | | |
|---|---|---|---|---|
| Thr | ACA | 126.00 | 3.28 | 0.06 |
| Thr | ACT | 1129.00 | 29.42 | 0.50 |
| Thr | ACC | 962.00 | 25.07 | 0.43 |
| Trp | TGG | 325.00 | 8.47 | 1.00 |
| End | TGA | 10.00 | 0.26 | 0.09 |
| Cys | TGT | 254.00 | 6.62 | 0.89 |
| Cys | TGC | 33.00 | 0.86 | 0.11 |
| End | TAG | 11.00 | 0.29 | 0.10 |
| End | TAA | 85.00 | 2.21 | 0.80 |
| Tyr | TAT | 219.00 | 5.71 | 0.19 |
| Tyr | TAC | 913.00 | 23.79 | 0.81 |
| Leu | TTG | 2202.00 | 57.38 | 0.69 |
| Leu | TTA | 576.00 | 15.01 | 0.18 |
| Phe | TTT | 432.00 | 11.26 | 0.27 |
| Phe | TTC | 1145.00 | 29.83 | 0.73 |
| Ser | TCG | 26.00 | 0.68 | 0.01 |
| Ser | TCA | 149.00 | 3.88 | 0.06 |
| Ser | TCT | 1279.00 | 33.33 | 0.52 |
| Ser | TCC | 818.00 | 21.31 | 0.33 |
| Arg | CGG | 0.00 | 0.00 | 0.00 |
| Arg | CGA | 1.00 | 0.03 | 0.00 |
| Arg | CGT | 249.00 | 6.49 | 0.15 |
| Arg | CGC | 5.00 | 0.13 | 0.00 |
| Gln | CAG | 62.00 | 1.62 | 0.05 |
| Gln | CAA | 1225.00 | 31.92 | 0.95 |
| His | CAT | 236.00 | 6.15 | 0.35 |
| His | CAC | 433.00 | 11.28 | 0.65 |
| Leu | CTG | 52.00 | 1.35 | 0.02 |
| Leu | CTA | 236.00 | 6.15 | 0.07 |
| Leu | CTT | 90.00 | 2.35 | 0.03 |
| Leu | CTC | 14.00 | 0.36 | 0.00 |
| Pro | CCG | 10.00 | 0.26 | 0.01 |
| Pro | CCA | 1271.00 | 33.12 | 0.80 |
| Pro | CCT | 279.00 | 7.27 | 0.18 |
| Pro | CCC | 33.00 | 0.86 | 0.02 |

*Fig. 7B*

Codon usage for Drosophila (highly expressed) genes

| AmAcid | Codon | Number | /1000 | Fraction |
|---|---|---|---|---|
| Gly | GGG | 6.00 | 0.28 | 0.00 |
| Gly | GGA | 380.00 | 18.04 | 0.22 |
| Gly | GGT | 575.00 | 27.29 | 0.34 |
| Gly | GGC | 746.00 | 35.41 | 0.44 |
| Glu | GAG | 1217.00 | 57.77 | 0.91 |
| Glu | GAA | 115.00 | 5.46 | 0.09 |
| Asp | GAT | 503.00 | 23.88 | 0.43 |
| Asp | GAC | 654.00 | 31.04 | 0.57 |
| Val | GTG | 719.00 | 34.13 | 0.45 |
| Val | GTA | 29.00 | 1.38 | 0.02 |
| Val | GTT | 226.00 | 10.73 | 0.14 |
| Val | GTC | 608.00 | 28.86 | 0.38 |
| Ala | GCG | 94.00 | 4.46 | 0.05 |
| Ala | GCA | 80.00 | 3.80 | 0.04 |
| Ala | GCT | 446.00 | 21.17 | 0.24 |
| Ala | GCC | 1277.00 | 60.61 | 0.67 |
| Arg | AGG | 48.00 | 2.28 | 0.06 |
| Arg | AGA | 12.00 | 0.57 | 0.01 |
| Ser | AGT | 16.00 | 0.76 | 0.01 |
| Ser | AGC | 267.00 | 12.67 | 0.23 |
| Lys | AAG | 1360.00 | 64.55 | 0.93 |
| Lys | AAA | 108.00 | 5.13 | 0.07 |
| Asn | AAT | 127.00 | 6.03 | 0.13 |
| Asn | AAC | 878.00 | 41.67 | 0.87 |
| Met | ATG | 387.00 | 18.37 | 1.00 |
| Ile | ATA | 4.00 | 0.19 | 0.00 |
| Ile | ATT | 390.00 | 18.51 | 0.29 |
| Ile | ATC | 969.00 | 45.99 | 0.71 |

*Fig. 8A*

| | | | | |
|---|---|---|---|---|
| Thr | ACG | 114.00 | 5.41 | 0.08 |
| Thr | ACA | 34.00 | 1.61 | 0.02 |
| Thr | ACT | 164.00 | 7.78 | 0.11 |
| Thr | ACC | 1127.00 | 53.49 | 0.78 |
| | | | | |
| Trp | TGG | 243.00 | 11.53 | 1.00 |
| End | TGA | 1.00 | 0.05 | 0.01 |
| Cys | TGT | 20.00 | 0.95 | 0.08 |
| Cys | TGC | 220.00 | 10.44 | 0.92 |
| | | | | |
| End | TAG | 12.00 | 0.57 | 0.17 |
| End | TAA | 58.00 | 2.75 | 0.82 |
| Tyr | TAT | 113.00 | 5.36 | 0.16 |
| Tyr | TAC | 574.00 | 27.25 | 0.84 |
| | | | | |
| Leu | TTG | 210.00 | 9.97 | 0.12 |
| Leu | TTA | 9.00 | 0.43 | 0.01 |
| Phe | TTT | 62.00 | 2.94 | 0.09 |
| Phe | TTC | 635.00 | 30.14 | 0.91 |
| | | | | |
| Ser | TCG | 195.00 | 9.26 | 0.17 |
| Ser | TCA | 29.00 | 1.38 | 0.02 |
| Ser | TCT | 103.00 | 4.89 | 0.09 |
| Ser | TCC | 558.00 | 26.49 | 0.48 |
| | | | | |
| Arg | CGG | 7.00 | 0.33 | 0.01 |
| Arg | CGA | 25.00 | 1.19 | 0.03 |
| Arg | CGT | 281.00 | 13.34 | 0.34 |
| Arg | CGC | 465.00 | 22.07 | 0.55 |
| | | | | |
| Gln | CAG | 703.00 | 33.37 | 0.91 |
| Gln | CAA | 66.00 | 3.13 | 0.09 |
| His | CAT | 88.00 | 4.18 | 0.22 |
| His | CAC | 312.00 | 14.81 | 0.78 |
| | | | | |
| Leu | CTG | 1182.00 | 56.10 | 0.69 |
| Leu | CTA | 21.00 | 1.00 | 0.01 |
| Leu | CTT | 55.00 | 2.61 | 0.03 |
| Leu | CTC | 224.00 | 10.63 | 0.13 |
| | | | | |
| Pro | CCG | 84.00 | 3.99 | 0.09 |
| Pro | CCA | 135.00 | 6.41 | 0.15 |
| Pro | CCT | 72.00 | 3.42 | 0.08 |
| Pro | CCC | 626.00 | 29.71 | 0.68 |

*Fig. 8B*

Codon usage for enteric bacterial (highly expressed) genes

| AmAcid | Codon | Number | /1000 | Fraction . . |
|---|---|---|---|---|
| Gly | GGG | 13.00 | 1.89 | 0.02 |
| Gly | GGA | 3.00 | 0.44 | 0.00 |
| Gly | GGU | 365.00 | 52.99 | 0.59 |
| Gly | GGC | 238.00 | 34.55 | 0.38 |
| Glu | GAG | 108.00 | 15.68 | 0.22 |
| Glu | GAA | 394.00 | 57.20 | 0.78 |
| Asp | GAU | 149.00 | 21.63 | 0.33 |
| Asp | GAC | 298.00 | 43.26 | 0.67 |
| Val | GUG | 93.00 | 13.50 | 0.16 |
| Val | GUA | 146.00 | 21.20 | 0.26 |
| Val | GUU | 289.00 | 41.96 | 0.51 |
| Val | GUC | 38.00 | 5.52 | 0.07 |
| Ala | GCG | 161.00 | 23.37 | 0.26 |
| Ala | GCA | 173.00 | 25.12 | 0.28 |
| Ala | GCU | 212.00 | 30.78 | 0.35 |
| Ala | GCC | 62.00 | 9.00 | 0.10 |
| Arg | AGG | 1.00 | 0.15 | 0.00 |
| Arg | AGA | 0.00 | 0.00 | 0.00 |
| Ser | AGU | 9.00 | 1.31 | 0.03 |
| Ser | AGC | 71.00 | 10.31 | 0.20 |
| Lys | AAG | 111.00 | 16.11 | 0.26 |
| Lys | AAA | 320.00 | 46.46 | 0.74 |
| Asn | AAU | 19.00 | 2.76 | 0.06 |
| Asn | AAC | 274.00 | 39.78 | 0.94 |
| Met | AUG | 170.00 | 24.68 | 1.00 |
| Ile | AUA | 1.00 | 0.15 | 0.00 |
| Ile | AUU | 70.00 | 10.16 | 0.17 |
| Ile | AUC | 345.00 | 50.09 | 0.83 |
| Thr | ACG | 25.00 | 3.63 | 0.07 |
| Thr | ACA | 14.00 | 2.03 | 0.04 |
| Thr | ACU | 130.00 | 18.87 | 0.35 |

*Fig. 9A*

| AmAcid | Codon | Number | /1000 | Fraction .. |
|--------|-------|--------|-------|-------------|
| Thr | ACC | 206.00 | 29.91 | 0.55 |
| Trp | UGG | 55.00 | 7.98 | 1.00 |
| End | UGA | 0.00 | 0.00 | 0.00 |
| Cys | UGU | 22.00 | 3.19 | 0.49 |
| Cys | UGC | 23.00 | 3.34 | 0.51 |
| End | UAG | 0.00 | 0.00 | 0.00 |
| End | UAA | 0.00 | 0.00 | 0.00 |
| Tyr | UAU | 51.00 | 7.40 | 0.25 |
| Tyr | UAC | 157.00 | 22.79 | 0.75 |
| Leu | UUG | 18.00 | 2.61 | 0.03 |
| Leu | UUA | 12.00 | 1.74 | 0.02 |
| Phe | UUU | 51.00 | 7.40 | 0.24 |
| Phe | UUC | 166.00 | 24.10 | 0.76 |
| Ser | UCG | 14.00 | 2.03 | 0.04 |
| Ser | UCA | 7.00 | 1.02 | 0.02 |
| Ser | UCU | 120.00 | 17.42 | 0.34 |
| Ser | UCC | 131.00 | 19.02 | 0.37 |
| Arg | CGG | 1.00 | 0.15 | 0.00 |
| Arg | CGA | 2.00 | 0.29 | 0.01 |
| Arg | CGU | 290.00 | 42.10 | 0.74 |
| Arg | CGC | 96.00 | 13.94 | 0.25 |
| Gln | CAG | 233.00 | 33.83 | 0.86 |
| Gln | CAA | 37.00 | 5.37 | 0.14 |
| His | CAU | 18.00 | 2.61 | 0.17 |
| His | CAC | 85.00 | 12.34 | 0.83 |
| Leu | CUG | 480.00 | 69.69 | 0.83 |
| Leu | CUA | 2.00 | 0.29 | 0.00 |
| Leu | CUU | 25.00 | 3.63 | 0.04 |
| Leu | CUC | 38.00 | 5.52 | 0.07 |
| Pro | CCG | 190.00 | 27.58 | 0.77 |
| Pro | CCA | 36.00 | 5.23 | 0.15 |
| Pro | CCU | 19.00 | 2.76 | 0.08 |
| Pro | CCC | 1.00 | 0.15 | 0.00 |

*Fig. 9B*

SEQUENCE LISTING

<160> NUMBER OF SEQ ID NOS: 17

<210> SEQ ID NO 1
<211> LENGTH: 659
<212> TYPE: DNA
<213> ORGANISM: Mus musculus
<220> FEATURE:
<221> NAME/KEY: CDS
<222> LOCATION: (14)...(646)

<400> SEQUENCE: 1

```
gagcgcagcc ctg atg gaa tgg atg aga tct aga gtt ggg acc ctg gga         49
            Met Glu Trp Met Arg Ser Arg Val Gly Thr Leu Gly
             1               5                  10 ctg tgg gtc cga ctg ctg ctg gct gtc ttc ctg ctg ggg gtc tac caa         97
Leu Trp Val Arg Leu Leu Leu Ala Val Phe Leu Leu Gly Val Tyr Gln
         15                  20                  25 gca tac ccc atc cct gac tcc agc ccc ctc ctc cag ttt ggg ggt caa       145
Ala Tyr Pro Ile Pro Asp Ser Ser Pro Leu Leu Gln Phe Gly Gly Gln
 30                  35                  40 gtc cgg cag agg tac ctc tac aca gat gac gac caa gac act gaa gcc       193
Val Arg Gln Arg Tyr Leu Tyr Thr Asp Asp Asp Gln Asp Thr Glu Ala
 45                  50                  55                  60 cac ctg gag atc agg gag gat gga aca gtg gta ggc gca gca cac cgc       241
His Leu Glu Ile Arg Glu Asp Gly Thr Val Val Gly Ala Ala His Arg
                 65                  70                  75 agt cca gaa agt ctc ctg gag ctc aaa gcc ttg aag cca ggg gtc att       289
Ser Pro Glu Ser Leu Leu Glu Leu Lys Ala Leu Lys Pro Gly Val Ile
             80                  85                  90 caa atc ctg ggt gtc aaa gcc tct agg ttt ctt tgc caa cag cca gat       337
Gln Ile Leu Gly Val Lys Ala Ser Arg Phe Leu Cys Gln Gln Pro Asp
         95                  100                 105 gga gct ctc tat gga tcg cct cac ttt gat cct gag gcc tgc agc ttc       385
Gly Ala Leu Tyr Gly Ser Pro His Phe Asp Pro Glu Ala Cys Ser Phe
 110                 115                 120 aga gaa ctg ctg ctg gag gac ggt tac aat gtg tac cag tct gaa gcc       433
Arg Glu Leu Leu Leu Glu Asp Gly Tyr Asn Val Tyr Gln Ser Glu Ala
125                 130                 135                 140 cat ggc ctg ccc ctg cgt ctg cct cag aag gac tcc cca aac cag gat       481
His Gly Leu Pro Leu Arg Leu Pro Gln Lys Asp Ser Pro Asn Gln Asp
                 145                 150                 155 gca aca tcc tgg gga cct gtg cgc ttc ctg ccc atg cca ggc ctg ctc       529
Ala Thr Ser Trp Gly Pro Val Arg Phe Leu Pro Met Pro Gly Leu Leu
             160                 165                 170 cac gag ccc caa gac caa gca gga ttc ctg ccc cca gag ccc cca gat       577
His Glu Pro Gln Asp Gln Ala Gly Phe Leu Pro Pro Glu Pro Pro Asp
         175                 180                 185 gtg ggc tcc tct gac ccc ctg agc atg gta gag cct tta cag ggc cga       625
Val Gly Ser Ser Asp Pro Leu Ser Met Val Glu Pro Leu Gln Gly Arg
```

```
                                    190                195                200
agc ccc agc tat gcg tcc tga ctcttcctga atc                                        659
Ser Pro Ser Tyr Ala Ser  *
205                 210

<210> SEQ ID NO 2
<211> LENGTH: 210
<212> TYPE: PRT
<213> ORGANISM: Mus musculus

<400> SEQUENCE: 2

Met Glu Trp Met Arg Ser Arg Val Gly Thr Leu Gly Leu Trp Val Arg
 1               5                  10                  15

Leu Leu Leu Ala Val Phe Leu Leu Gly Val Tyr Gln Ala Tyr Pro Ile
            20                  25                  30

Pro Asp Ser Ser Pro Leu Leu Gln Phe Gly Gly Gln Val Arg Gln Arg
            35                  40                  45

Tyr Leu Tyr Thr Asp Asp Gln Asp Thr Glu Ala His Leu Glu Ile
 50                  55                  60

Arg Glu Asp Gly Thr Val Val Gly Ala Ala His Arg Ser Pro Glu Ser
65                   70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
            100                 105                 110

Gly Ser Pro His Phe Asp Pro Glu Ala Cys Ser Phe Arg Glu Leu Leu
            115                 120                 125

Leu Glu Asp Gly Tyr Asn Val Tyr Gln Ser Glu Ala His Gly Leu Pro
130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Pro Glu Pro Pro Asp Val Gly Ser Ser
            180                 185                 190

Asp Pro Leu Ser Met Val Glu Pro Leu Gln Gly Arg Ser Pro Ser Tyr
            195                 200                 205

Ala Ser
    210

<210> SEQ ID NO 3
<211> LENGTH: 643
<212> TYPE: DNA
<213> ORGANISM: Homo sapiens
<220> FEATURE:
<221> NAME/KEY: CDS
<222> LOCATION: (9)...(638)

<400> SEQUENCE: 3 agccattg atg gac tcg gac gag acc ggg ttc gag cac tca gga ctg tgg    50
        Met Asp Ser Asp Glu Thr Gly Phe Glu His Ser Gly Leu Trp
         1               5                  10 gtt tct gtg ctg gct ggt ctt ctg ctg gga gcc tgc cag gca cac ccc    98
Val Ser Val Leu Ala Gly Leu Leu Leu Gly Ala Cys Gln Ala His Pro
 15                  20                  25                  30 atc cct gac tcc agt cct ctc ctg caa ttc ggg ggc caa gtc cgg cag   146
Ile Pro Asp Ser Ser Pro Leu Leu Gln Phe Gly Gly Gln Val Arg Gln
                35                  40                  45
```

|  |  |  |  |  |  |  |  |  |  |  |  |  |  |  |  |
|---|---|---|---|---|---|---|---|---|---|---|---|---|---|---|---|
| cgg | tac | ctc | tac | aca | gat | gat | gcc | cag | cag | aca | gaa | gcc | cac | ctg | gag | 194
| Arg | Tyr | Leu | Tyr | Thr | Asp | Asp | Ala | Gln | Gln | Thr | Glu | Ala | His | Leu | Glu |
|  |  | 50 |  |  |  | 55 |  |  |  | 60 |  |  |  |  |  |

```
cgg tac ctc tac aca gat gat gcc cag cag aca gaa gcc cac ctg gag      194
Arg Tyr Leu Tyr Thr Asp Asp Ala Gln Gln Thr Glu Ala His Leu Glu
         50                  55                  60 atc agg gag gat ggg acg gtg ggg ggc gct gct gac cag agc ccc gaa      242
Ile Arg Glu Asp Gly Thr Val Gly Gly Ala Ala Asp Gln Ser Pro Glu
 65                  70                  75 agt ctc ctg cag ctg aaa gcc ttg aag ccg gga gtt att caa atc ttg      290
Ser Leu Leu Gln Leu Lys Ala Leu Lys Pro Gly Val Ile Gln Ile Leu
     80                  85                  90 gga gtc aag aca tcc agg ttc ctg tgc cag cgg cca gat ggg gcc ctg      338
Gly Val Lys Thr Ser Arg Phe Leu Cys Gln Arg Pro Asp Gly Ala Leu
 95                 100                 105                 110 tat gga tcg ctc cac ttt gac cct gag gcc tgc agc ttc cgg gag ctg      386
Tyr Gly Ser Leu His Phe Asp Pro Glu Ala Cys Ser Phe Arg Glu Leu
                115                 120                 125 ctt ctt gag gac gga tac aat gtt tac cag tcc gaa gcc cac ggc ctc      434
Leu Leu Glu Asp Gly Tyr Asn Val Tyr Gln Ser Glu Ala His Gly Leu
                130                 135                 140 ccg ctg cac ctg cca ggg aac aag tcc cca cac cgg gac cct gca ccc      482
Pro Leu His Leu Pro Gly Asn Lys Ser Pro His Arg Asp Pro Ala Pro
                145                 150                 155 cga gga cca gct cgc ttc ctg cca cta cca ggc ctg ccc ccc gca ctc      530
Arg Gly Pro Ala Arg Phe Leu Pro Leu Pro Gly Leu Pro Pro Ala Leu
160                 165                 170 ccg gag cca ccc gga atc ctg gcc ccc cag ccc ccc gat gtg ggc tcc      578
Pro Glu Pro Pro Gly Ile Leu Ala Pro Gln Pro Pro Asp Val Gly Ser
175                 180                 185                 190 tcg gac cct ctg agc atg gtg gga cct tcc cag ggc cga agc ccc agc      626
Ser Asp Pro Leu Ser Met Val Gly Pro Ser Gln Gly Arg Ser Pro Ser
                195                 200                 205 tac gct tcc tga agcca                                                643
Tyr Ala Ser  *
```

<210> SEQ ID NO 4
<211> LENGTH: 209
<212> TYPE: PRT
<213> ORGANISM: Homo sapiens

<400> SEQUENCE: 4

```
Met Asp Ser Asp Glu Thr Gly Phe Glu His Ser Gly Leu Trp Val Ser
 1               5                  10                  15

Val Leu Ala Gly Leu Leu Gly Ala Cys Gln Ala His Pro Ile Pro
             20                  25                  30

Asp Ser Ser Pro Leu Leu Gln Phe Gly Gly Gln Val Arg Gln Arg Tyr
         35                  40                  45

Leu Tyr Thr Asp Ala Gln Gln Thr Glu Ala His Leu Glu Ile Arg
     50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
```

-continued

```
                145                 150                 155                 160
Pro Ala Arg Phe Leu Pro Leu Pro Gly Leu Pro Pro Ala Leu Pro Glu
                    165                 170                 175
Pro Pro Gly Ile Leu Ala Pro Gln Pro Pro Asp Val Gly Ser Ser Asp
            180                 185                 190
Pro Leu Ser Met Val Gly Pro Ser Gln Gly Arg Ser Pro Ser Tyr Ala
        195                 200                 205
Ser

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
agccattgat ggactcggac                                              20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
tggcttcagg aagcgtagct                                              20

<210> SEQ ID NO 7
<211> LENGTH: 16
<212> TYPE: PRT
<213> ORGANISM: Homo sapiens

<400> SEQUENCE: 7

Arg Gln Arg Tyr Leu Tyr Thr Asp Asp Ala Gln Gln Thr Glu Ala His
1               5                   10                  15

<210> SEQ ID NO 8
<211> LENGTH: 15
<212> TYPE: PRT
<213> ORGANISM: Homo sapiens

<400> SEQUENCE: 8

His Leu Pro Gly Asn Lys Ser Pro His Arg Asp Pro Ala Pro Arg
1               5                   10                  15

<210> SEQ ID NO 9
<211> LENGTH: 218
<212> TYPE: PRT
<213> ORGANISM: Mus musculus

<400> SEQUENCE: 9

Met Ala Arg Lys Trp Asn Gly Arg Ala Val Ala Arg Ala Leu Val Leu
1               5                   10                  15

Ala Thr Leu Trp Leu Ala Val Ser Gly Arg Pro Leu Ala Gln Gln Ser
                20                  25                  30

Gln Ser Val Ser Asp Glu Asp Pro Leu Phe Leu Tyr Gly Trp Gly Lys
            35                  40                  45

Ile Thr Arg Leu Gln Tyr Leu Tyr Ser Ala Gly Pro Tyr Val Ser Asn
        50                  55                  60
```

-continued

```
Cys Phe Leu Arg Ile Arg Ser Asp Gly Ser Val Asp Cys Glu Glu Asp
 65                  70                  75                  80

Gln Asn Glu Arg Asn Leu Leu Glu Phe Arg Ala Val Ala Leu Lys Thr
                 85                  90                  95

Ile Ala Ile Lys Asp Val Ser Val Arg Tyr Leu Cys Met Ser Ala
            100                 105                 110

Asp Gly Lys Ile Tyr Gly Leu Ile Arg Tyr Ser Glu Glu Asp Cys Thr
            115                 120                 125

Phe Arg Glu Glu Met Asp Cys Leu Gly Tyr Asn Gln Tyr Arg Ser Met
130                 135                 140

Lys His His Leu His Ile Ile Phe Ile Gln Ala Lys Pro Arg Glu Gln
145                 150                 155                 160

Leu Gln Asp Gln Lys Pro Ser Asn Phe Ile Pro Val Phe His Arg Ser
                165                 170                 175

Phe Phe Glu Thr Gly Asp Gln Leu Arg Ser Lys Met Phe Ser Leu Pro
                180                 185                 190

Leu Glu Ser Asp Ser Met Asp Pro Phe Arg Met Val Glu Asp Val Asp
            195                 200                 205

His Leu Val Lys Ser Pro Ser Phe Gln Lys
        210                 215

<210> SEQ ID NO 10
<211> LENGTH: 216
<212> TYPE: PRT
<213> ORGANISM: Homo sapiens

<400> SEQUENCE: 10

Met Arg Ser Gly Cys Val Val His Val Trp Ile Leu Ala Gly Leu
 1               5                  10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
             35                  40                  45

Thr Ser Gly Pro His Gly Leu Ser Ser Cys Phe Leu Arg Ile Arg Ala
         50                  55                  60

Asp Gly Val Val Asp Cys Ala Arg Gly Gln Ser Ala His Ser Leu Leu
 65                  70                  75                  80

Glu Ile Lys Ala Val Ala Leu Arg Thr Val Ala Ile Lys Gly Val His
                 85                  90                  95

Ser Val Arg Tyr Leu Cys Met Gly Ala Asp Gly Lys Met Gln Gly Leu
             100                 105                 110

Leu Gln Tyr Ser Glu Glu Asp Cys Ala Phe Glu Glu Glu Ile Arg Pro
         115                 120                 125

Asp Gly Tyr Asn Val Tyr Arg Ser Glu Lys His Arg Leu Pro Val Ser
130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
            195                 200                 205

Val Arg Ser Pro Ser Phe Glu Lys
        210                 215
```

<210> SEQ ID NO 11
<211> LENGTH: 10
<212> TYPE: PRT
<213> ORGANISM: Unknown
<220> FEATURE:
<223> OTHER INFORMATION: Residues which contain the anitgenic
      determinant recognized by the myc monoclonal antibody.

<400> SEQUENCE: 11

Glu Gln Lys Leu Ile Ser Glu Glu Asp Leu
1               5                   10

<210> SEQ ID NO 12
<211> LENGTH: 5
<212> TYPE: PRT
<213> ORGANISM: Unknown
<220> FEATURE:
<223> OTHER INFORMATION: Preferred thrombin cleave site.

<400> SEQUENCE: 12

Leu Val Pro Arg Gly
1               5

<210> SEQ ID NO 13
<211> LENGTH: 10
<212> TYPE: PRT
<213> ORGANISM: Unknown
<220> FEATURE:
<223> OTHER INFORMATION: Residues which bind to paramagnetic
      streptavidin beads (used for purification).

<400> SEQUENCE: 13

Ser Ala Trp Arg His Pro Gln Phe Gly Gly
1               5                   10

<210> SEQ ID NO 14
<211> LENGTH: 7
<212> TYPE: PRT
<213> ORGANISM: Homo sapiens

<400> SEQUENCE: 14

Arg Pro Tyr Asp Gly Tyr Asn
1               5

<210> SEQ ID NO 15
<211> LENGTH: 6
<212> TYPE: PRT
<213> ORGANISM: Homo sapiens

<400> SEQUENCE: 15

Leu Pro Met Leu Pro Met
1               5

<210> SEQ ID NO 16
<211> LENGTH: 6
<212> TYPE: PRT
<213> ORGANISM: Homo sapiens

<400> SEQUENCE: 16

Arg Pro Asp Gly Tyr Asn
1               5

<210> SEQ ID NO 17
<211> LENGTH: 6
<212> TYPE: PRT

-continued

```
<213> ORGANISM: Homo sapiens

<400> SEQUENCE: 17

His Phe Leu Pro Met Leu
1               5
```

HUMAN FGF-21 POLYPEPTIDES

CROSS-REFERENCE TO RELATED APPLICATIONS

This application is a divisional application of U.S. patent application Ser. No. 09/715,805, filed Nov. 16, 2000, issued as U.S. Pat. No. 6,716,626, which claims priority from U.S. Provisional patent application Ser. No. 60/166,540 filed Nov. 18, 1999 and U.S. Provisional patent application Ser. No. 60/203,633 filed May 11, 2000, which are incorporated by reference herein in their entirety.

TECHNICAL FIELD

The present invention relates to nucleic acid sequences encoding a member of the fibroblast growth factor (FGF) family, and to polypeptides encoded by the nucleic acid sequence.

BACKGROUND OF THE INVENTION

The prototypic fibroblast growth factors (FGFs), FGF-1 and FGF-2, were originally isolated from brain and pituitary as mitogens for fibroblasts. However, FGF-1 and FGF-2 are widely expressed in developing and adult tissues, and are polypeptides with multiple biological activities including angiogenesis, mitogenesis, cellular differentiation and repair of tissue injury (Baird, A. et al., *Cancer Cells* 3:239–243 (1991); Burgess, W. H. et al., *Annu. Rev. Biochem.* 58:575–606 (1989). According to the published literature, the FGF family now consists of at least nineteen members, FGF-1 to FGF-19. FGF-3 was identified to be a common target for activation by the mouse mammary tumor virus (Dickson et al., *Ann. N.Y. Acad. Sci.* 638:18–26 (1991); FGF-4 to FGF-6 were identified as oncogene products (Yoshida et al., *Ann. NY Acad. Sci.* 638:27–37 (1991); Goldfarb et al., *Ann. NY Acad. Sci* 638:38–52 (1991); Coulier et al., *Ann. NY Acad. Sci.* 638:53–61 (1991)). FGF-10 was identified from rat lung by homology-based polymerase chain reaction (PCR) (Yamasaki et al., *J. Biol. Chem.* 271:15918–15921 (1996)). FGF-11 to FGF-14 (FGF homologous factors (FHFs) 1 to 4) were identified from human retina by a combination of random cDNA sequencing, data base searches and homology-based PCR (Smallwood et al., *Proc. Natl. Acad. Sci. USA* 93:9850–9857 (1996)). FGF-15 was identified as a downstream target of a chimeric homeodomain oncoprotein (McWhirter et al., *Development* 124:3221–3232 (1997)). FGF-16, FGF-17, and FGF-18 were identified from rat heart and embryos by homology-based PCR, respectively (Miyake et al., *Biochem. Biophys. Res. Commun.* 243:148–152 (1998); Hoshikawa et al., *Biochem. Biophys. Res. Commun.* 244:187–191 (1998); Ohbayashi et al., *J. Biol. Chem.* 273:18161–18164 (1998)). Recently, FGF-19 was identified from human fetal brain by data base search (Nishimura et al., *Biochim. Biophys. Acta* 1444:148–151 (1999)). They have a conserved ~120-amino acid residue core with ~30 to 60% amino acid identity. These FGFs also appear to play important roles in both developing and adult tissues. Thus, there is a need in the art for additional FGF molecules having functions and activities that differ from the known FGFs and for FGF molecules specifically expressed in tissues implicated in human disease.

SUMMARY OF THE INVENTION

The present invention provides a composition comprising an isolated polynucleotide selected from the group consisting of:

(a) a polynucleotide comprising at least eight contiguous nucleotides of SEQ ID NO:1 or 3;

(b) a polynucleotide having at least 80% homology to the polynucleotide of (a); and (c) a polynucleotide encoding a protein expressed by a polynucleotide having the sequence of SEQ ID NO:1 or 3.

The invention further provides for the use of the isolated polynucleotides or fragments thereof as diagnostic probes or as primers.

The present invention also provides a composition comprising a polypeptide, wherein said polypeptide is selected from the group consisting of:

(a) a polypeptide comprising at least 6 contiguous amino acids encoded by SEQ ID NO:1 or 3;

(b) a polypeptide encoded by a polynucleotide comprising SEQ ID NO:1 or 3; and (c) a variant of the polypeptide of SEQ ID NO:2 or 4.

In certain preferred embodiments of the invention, the polynucleotide is operably linked to an expression control sequence. The invention further provides a host cell, including bacterial, yeast, insect and mammalian cells, transformed with the polynucleotide sequence. The invention also provides full-length cDNA and full-length polynucleotides corresponding to SEQ ID NO:1 or 3.

Protein and polypeptide compositions of the invention may further comprise a pharmaceutically acceptable carrier. Compositions comprising an antibody that specifically reacts with such protein or polypeptide are also provided by the present invention.

The invention also provides for the production of large amounts of otherwise minor cell populations of cells to be used for generation of cDNA libraries for the isolation of rare molecules expressed in the precursors cells or progeny; cells produced by treatment may directly express growth factors or other molecules, and conditioned media is screened in assays for novel activities.

The invention further provides for the isolation, self-renewal and survival of mammalian stem cells and the differentiation of their progeny.

The invention also provides for compositions and methods of preventing or slowing the degeneration of or increasing the numbers of hepatic cells, in disease states including but not limited to, cirrhosis of the liver, hepatitis, and post-surgical and post-injury tissue regeneration; of preventing or slowing degeneration of or increasing the numbers of cells in the testes in disease states such as infertility and impotence, and of preventing or slowing degeneration of or increasing the numbers of cells of the thymus in disorders of the thymus and immune system.

The invention also provides for compositions and methods for identifying inhibitors of FGF-21 function, useful in disease states such as liver and testicular cancers, or leukemias, lymphomas or other cancers, and proliferative or differentiation disorders of cells derived from the thymus.

BRIEF DESCRIPTION OF THE DRAWINGS

FIG. 1. Amino acid sequence comparison of human FGF-21 with mouse FGF-15. Asterisks indicate identical amino acid residues of the sequences.

FIG. 2. Amino acid sequence comparison of human FGF-21 and human FGF-19. Asterisks indicate identical amino acid residues of the sequences.

FIG. 4A–4B. DNA sequence (SEQ ID NO:1) and amino acid sequence (SEQ ID NO:2) of mouse FGF-21.

FIG. 5A–5B. DNA sequence (SE ID NO:3) and amino acid sequence (SEQ ID NO:4) of human FGF-21

FIG. 6. Alignment of the amino acid sequences of human (SEQ ID NO:4) and mouse (SEQ ID NO:2) FGF-21.

FIG. 7A–7B. FIG. 7A–7B provides codon usage for yeast. The first field of information on each line of the table contains a three-letter code for an amino acid. The second field contains an unambiguous codon for that amino acid. The third field lists the number of occurrences of that codon in the genes from which the table is compiled. The fourth field lists the expected number of occurrences of that codon per 1,000 codons in genes whose codon usage is identical to that compiled in the codon frequency table. The last field contains the fraction of occurrences of the codon in its synonymous codon family.

FIG. 8A–8B. FIG. 8A–8B provides codon usage for *Drosophila*.

FIG. 9A–9B. FIG. 9A–9B provides codon usage for *E. coli*.

DETAILED DESCRIPTION OF THE INVENTION

Figure 3:
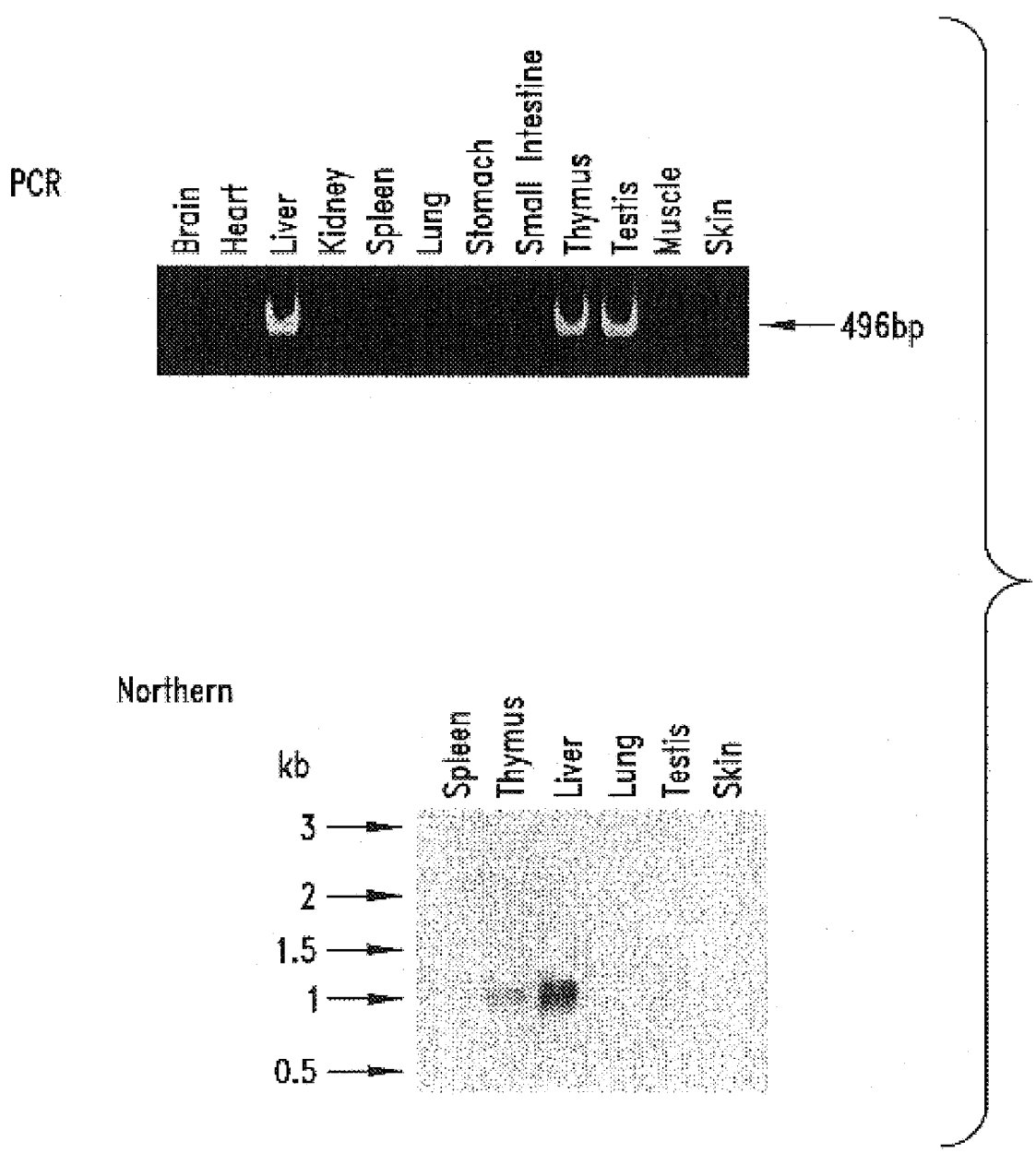
FIG. 3. Expression of FGF-21 in mouse tissues.

Because of their potent activities for promoting growth, proliferation, survival and differentiation of a wide variety of cells and tissue types, FGFs continue to be pursued as therapeutic agents for a number of different indications, including wound healing, such as musculo-skeletal conditions, for example, bone fractures, ligament and tissue repair, tendonitis, bursitis, etc.; skin conditions, for example, burns, cuts, lacerations, bed sores, slow healing ulcers, etc.; tissue protection, repair, and the induction of angiogenesis during myocardial infarction and ischemia, in the treatment of neurological conditions, for example, neuro-degenerative disease and stroke, in the treatment of eye disease, including macular degeneration, and the like.

The fibroblast growth factor (FGF) proteins identified to date belong to a family of signaling molecules that regulate growth and differentiation of a variety of cell types. The significance of FGF proteins to human physiology and pathology relates in part to their key roles in embryogenesis, in blood vessel development and growth, and in bone growth. In vitro experiments have demonstrated a role for FGF in regulating cell growth and division of endothelial cells, vascular smooth muscle cells, fibroblasts, and cardiac and skeletal myocytes. Other members of the FGF family and their biological roles are described in Crossley et al., *Development* 121:439–451 (1995); Ohuchi et al., *Development* 124:2235–2244 (1997); Gemel et al., *Genomics* 35:253–257 (1996); and Ghosh et al., *Cell Growth and Differentiation* 7:1425–1434 (1996).

FGF proteins are also significant to human health and disease because of a role in cancer cell growth. For example, FGF-8 was identified as an androgen-induced growth factor in breast and prostate cancer cells. (Tanaka et al., *FEBS Lett.* 363:226–230 (1995) and *P.N.A.S.* 89:8928–8932 (1992)).

The role of FGF in normal development is being elucidated in part through studies of FGF receptors. Wilke, T. et al., *Dev. Dynam.* 210:41–52 (1997) found that FGFR1, FGFR2, and FGFR3 transcripts were localized to specific regions of the head during embryonic development in chickens. The expression pattern correlated with areas affected by human FGFR mutations in Crouzon syndrome, a condition of abnormal intramembranous bone formation. Belluardo, N. et al., *Jour. Comp. Neur.* 379:226–246 (1997) studied localization of FGFR 1, 2, and 3 mRNAs in rat brain, and found cellular specificity in several brain regions. Furthermore, FGFR1 and FGFR2 mRNAs were expressed in astroglial reactive cells after brain lesion, supporting a role of certain FGF's in brain disease and injury. Ozawa, K. et al., *Mol. Brain Res.* 41:279–288 (1996) reported that FGF1 and FGF-5 expression increased after birth, whereas FGF3, FGF-6, FGF-7, and FGF-8 genes showed higher expression in late embryonic stages than in postnatal stages.

New members of the FGF family are described here, wherein the FGF protein is expressed in a variety of tissues but most abundantly in the liver. A polynucleotide encoding the mouse FGF of the invention has the sequence as shown in SEQ ID NO:1. A polynucleotide encoding the human FGF of the invention has the sequence as shown in SEQ ID NO:3. The mouse polynucleotide was identified as encoding a member of the FGF family by the conserved regions throughout the amino acid sequence and by the regions of homology shared by the polynucleotide and genes encoding known FGF proteins.

The inventors believe that FGF-21 is a previously unidentified member of the FGF family. To date, over 19 human FGF proteins have been identified. In most cases, homologous proteins in other mammals, particularly mice and rats, have also been identified. The human proteins vary to different degrees in terms of amino acid sequence, receptor specificity, tissue expression patterns, and biological activity.

The present FGF-21 differs in sequence from all the FGF proteins described to date in publications. As discussed herein, the knowledge about the roles played by various FGF proteins continues to grow, but is by far incomplete.

The present invention adds to this knowledge by disclosing that the FGF of SEQ ID NO:1 is highly expressed in liver, and human FGF-21 may play a role in development of and recovery from liver disease. Further, FGF-21 is also expressed in testis and thymus, and therefore may play a role in the development or recovery from disorders of testicular function or function of cells derived from the thymus. The invention therefore is based upon the identification, isolation and sequencing of a new fibroblast growth factor (FGF-21).

Isolation and Analysis of Mouse cDNA Encoding FGF-21 According to the invention, DNA encoding a novel mouse FGF has been identified. The nucleotide sequence of the entire coding region was determined by adaptor-ligation mediated polymerase chain reaction using mouse embryo cDNA as a template. The nucleotide sequence of the coding region allowed for the elucidation of the complete amino acid sequence of the mouse FGF (210 amino acids) (FIG. 4). This protein is tentatively named FGF-21.

Isolation and Analysis of Human cDNA Encoding FGF-21 A human gene encoding FGF-21 was located in the 5' flanking region of a putative human α-fucosyltransferase gene. The cDNA encoding the entire coding region of human FGF-21 was amplified from fetal brain cDNA by PCR using FGF-specific primers as follows: sense primer: 5' agccattgatggactcggac 3' (SEQ ID NO:5); antisense primer: 5' tggcttcaggaagcgtagct 3' (SEQ ID NO:6).

Expression of FGF-21 mRNA in Adult Mouse Tissues The expression of FGF-21 mRNA was examined in adult mouse major tissues including brain, heart, lung, liver, kidney, spleen, lung, thymus, testis, muscle, skin, and small intestine by polymerase chain reaction. FGF-21 mRNA expression was detected at high levels in the liver (FIG. 3). Expression was also seen in testis and thymus. To confirm the expression of FGF-21 mRNA in mouse tissues, mouse tissue (A)+ RNA was examined by Northern blotting analysis using a $^{32}$P-labeled rat FGF-21 cDNA probe. The results confirmed a high level of expression in mouse liver. Expression was also seen in thymus; larger transcripts were seen in testis tissue.

Reference to FGF-21 herein is intended to be construed to include growth factors of any origin which are substantially homologous to and which are biologically equivalent to the FGF-21 characterized and described herein. Such substantially homologous growth factors may be native to any tissue or species and, similarly, biological activity can be characterized in any of a number of biological assay systems.

The term "biologically equivalent" is intended to mean that the compositions of the present invention are capable of demonstrating some or all of the same growth properties in a similar fashion, not necessarily to the same degree as the FGF-21 isolated as described herein or recombinantly produced human FGF-21 of the invention.

By "substantially homologous" it is meant that the degree of homology of human FGF-21 to FGF-21 from any species is greater than that between FGF-21 and any previously reported member of the FGF family.

Sequence identity or percent identity is intended to mean the percentage of same residues between two sequences, referenced to human FGF when determining percent identity with non-human FGF-21, referenced to FGF-21 when determining percent identity with non-FGF-21 growth factors, when the two sequences are aligned using the Clustal method (Higgins et al, Cabios 8:189–191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in Atlas of Protein Sequence and Structure, Dayhoff, Ed., NDRF, Washington, Vol. 5, suppl. 3, p. 345, 1978).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to human FGF-21 when determining percent conservation with non-human FGF-21, and referenced to FGF-21 when determining percent conservation with non-FGF-21 growth factors. Conservative amino acid changes satisfying this requirement are: R-K; E-D, Y-F, L-M; V-I, Q-H.

The invention provides FGF-21 proteins or variants thereof having one or more polymers covalently attached to one or more reactive amino acid side chains. By way of example, not limitation, such polymers include polyethylene glycol (PEG), which can be attached to one or more free cysteine sulfhydryl residues, thereby blocking the formation of disulfide bonds and aggregation when the protein is exposed to oxidizing conditions. In addition, pegylation of FGF-21 proteins and/or muteins is expected to provide such improved properties as increased half-life, solubility, and protease resistance. FGF-21 proteins and/or muteins may alternatively be modified by the covalent addition of polymers to free amino groups such as the lysine epsilon or the N-terminal amino group. Preferred cysteines and lysines for covalent modification will be those not involved in receptor or heparin binding or in proper protein folding. For example, cys 27 and cys 104 may be modified. It will be apparent to one skilled in the art that the methods for assaying FGF-21 biochemical and/or biological activity may be employed in order to determine if modification of a particular amino acid residue affects the activity of the protein as desired.

It may be advantageous to improve the stability of FGF-21 by modifying one or more protease cleavage sites. Thus, the present invention provides FGF-21 variants in which one or more protease cleavage site has been altered by, for example, substitution of one or more amino acids at the cleavage site in order to create an FGF-21 variant with improved stability. Such improved protein stability may be beneficial during protein production and/or therapeutic use. A preferred site is a monobasic site within two residues of a proline, such as near residue 160 of SEQ ID NO:4.

Suitable protease cleavage sites for modification are well known in the art and likely will vary depending on the particular application contemplated. For example, typical substitutions would include replacement of lysines or arginines with other amino acids such as alanine. The loss of activity, such as receptor binding or heparin binding, can be tested for as described herein.

FGF-21 can also include hybrid and modified forms of FGF-21 including fusion proteins and FGF-21 fragments and hybrid and modified forms in which certain amino acids have been deleted or replaced and modifications such as where one or more amino acids have been changed to a modified amino acid or unusual amino acid and modifications such as glycosylations so long as the hybrid or modified form retains the biological activity of FGF-21. Fusion proteins can consist of the FGF-21 of the invention or fragment thereof and a signal sequence of a heterologous protein to promote secretion of the protein product.

Fusion proteins comprising FGF-21 or a biologically active or antigenic fragment thereof can be produced using methods known in the art. Such fusion proteins can be used therapeutically or can be produced in order to simplify the isolation and purification procedures. Histidine residues can be incorporated to allow immobilized metal affinity chromatography purification. Residues EQKLISEEDL (SEQ ID NO:11) contain the antigenic determinant recognized by the myc monoclonal antibody and can be incorporated to allow myc monoclonal antibody-based affinity purification. A thrombin cleavage site can be incorporated to allow cleavage of the molecule at a chosen site; a preferred thrombin cleavage site consists of residues LVPRG. Purification of the molecule can be facilitated by incorporating a sequence, such as residues SAWRHPQFGG (SEQ ID NO:13), which binds to paramagnetic streptavidin beads. Such embodiments are described in WO 97/25345, which is incorporated by reference.

The invention further includes chimeric molecules between FGF-21 and keratinocyte growth factor (KGF)

(Reich-Slotky, R. et al., *J. Biol. Chem.* 270:29813–29818 (1995)). The chimeric molecule can contain specific regions or fragments of one or both of the FGF-21 and KGF molecules, such as the FGF-21 fragments described below.

The invention also includes fragments of FGF-21. Preferred fragments of SEQ ID NO:4 and 2, respectively, include: amino acids from about 1 to about 209 (210 for SEQ ID NO:2); amino acids from about 2 to about 209 (210 for SEQ ID NO:2); amino acids from about 1 to about 177; amino acids from about 40 to about 209 for SEQ ID NO:2 and amino acids from about 40 to about 177. Such fragments can be prepared from the proteins by standard biochemical methods, or by expressing a polynucleotide encoding the fragment.

FGF-21, or a fragment thereof, can be produced as a fusion protein comprising human serum albumin (HSA) or a portion thereof. Such fusion constructs are suitable for enhancing expression of the FGF-21, or fragment thereof, in an eukaryotic host cell. Exemplary HSA portions include the N-terminal polypeptide (amino acids 1–369, 1–419, and intermediate lengths starting with amino acid 1), as disclosed in U.S. Pat. No. 5,766,883, and publication WO 97/24445, incorporated by reference herein. Other chimeric polypeptides can include a HSA protein with FGF-21, or fragments thereof, attached to each of the C-terminal and N-terminal ends of the HSA. Such HSA constructs are disclosed in U.S. Pat. No. 5,876,969, incorporated by reference herein.

Also included with the scope of the invention are FGF-21 molecules that differ from native FGF-21 by virtue of changes in biologically active sites.

Growth factors are thought to act at specific receptors. According to the invention, FGF-21 and as yet unknown members of this family of growth factors act through specific receptors having distinct distributions as has been shown for other growth factor families.

A preferred hFGF-21 of the present invention has been identified. Also preferred is hFGF-21 prepared by recombinant DNA technology. Included within the scope of the invention are polynucleotides, including DNA and RNA, with 80% homology to SEQ ID NO:1 or SEQ ID NO:3; preferably at least 85% homology, more preferably at least 90% homology, most preferably 95% homology. Polynucleotides with 96%, 97%, 98%, and 99% homology to SEQ ID NO:1 or 3 are also included. Percent homology is calculated using methods known in the art. A non-limiting example of such a method is the Smith-Waterman homology search algorithm as implemented in MPSRCH program (Oxford Molecular), using an affine gap search with a gap open penalty of 12 and a gap extension penalty of 1.

FGF-21 can also include hybrid and modified forms of FGF-21 including fusion proteins and FGF-21 fragments and hybrid and modified forms in which certain amino acids have been deleted or replaced and modifications such as where one or more amino acids have been changed to a modified amino acid or unusual amino acid and modifications such as glycosylations so long as the hybrid or modified form retains the biological activity of FGF-21. By retaining the biological activity, it is meant that the ability of FGF-21 to promote the growth, survival or differentiation of responsive cells is preserved, although not necessarily at the same level of potency as that of the FGF-21 isolated as described herein or that of the recombinantly produced FGF-21.

Also included within the meaning of substantially homologous is any FGF-21 which may be isolated by virtue of cross-reactivity with antibodies to the FGF-21 described herein or whose encoding nucleotide sequences including genomic DNA, mRNA or cDNA may be isolated through hybridization with the complementary sequence of genomic or subgenomic nucleotide sequences or cDNA of the FGF-21 herein or fragments thereof. It will also be appreciated by one skilled in the art that degenerate DNA sequences can encode human FGF-21 and these are also intended to be included within the present invention as are allelic variants of FGF-21.

Recombinant human FGF-21 may be made by expressing the DNA sequences encoding FGF-21 in a suitable transformed host cell. Using methods well known in the art, the DNA encoding FGF-21 may be linked to an expression vector, transformed into a host cell and conditions established that are suitable for expression of FGF-21 by the transformed cell.

The DNA encoding FGF-21 can be engineered to take advantage of preferred codon usage of host cells. Codon usage in *Pseudomonas aeruginosa* is described in, for example, West et al., *Nucleic Acids Res.* 11:9323–9335 (1988). Codon usage in *Saccharomyces cerevisiae* is described in, for example, Lloyd et al., *Nucleic Acids Res.* 20:5289–5295 (1992). Codon preference in Corynebacteria and a comparison with *E. coli* preference is provided in Malubres et al., *Gene* 134:15–24 (1993). Codon usage in *Drosophila melanogaster* is described in, for example, Akashi, *Genetics* 136:927–935 (1994). Codon usage in yeast is also shown in FIG. 7, codon usage in *Drosophila* is shown in FIG. 8, and codon usage for *E. coli* is shown in FIG. 9.

Any suitable expression vector may be employed to produce recombinant human FGF-21 such as expression vectors for use in insect cells. Baculovirus expression systems can also be employed. A preferable method is expression in insect cells, such as Tr5 or Sf9 cells, using baculovirus vector.

The present invention includes nucleic acid sequences including sequences that encode human FGF-21. Also included within the scope of this invention are sequences that are substantially the same as the nucleic acid sequences encoding FGF-21. Such substantially the same sequences may, for example, be substituted with codons more readily expressed in a given host cell such as *E. coli* according to well known and standard procedures. Such modified nucleic acid sequences are included within the scope of this invention.

Specific nucleic acid sequences can be modified by those skilled in the art and, thus, all nucleic acid sequences that code for the amino acid sequences of FGF-21 can likewise be so modified. The present invention thus also includes nucleic acid sequence which will hybridize with all such nucleic acid sequences, or complements of the nucleic acid sequences where appropriate, and encode a polypeptide having the cell survival, growth or differentiation activity of FGF-21. The present invention also includes nucleic acid sequences that encode polypeptides that have cell survival promoting activity and that are recognized by antibodies that bind to FGF-21. Preferred methods and epitopes for raising antibodies are described in Example 4.

The present invention also encompasses vectors comprising expression regulatory elements operably linked to any of the nucleic acid sequences included within the scope of the invention. This invention also includes host cells of any variety that have been transformed with vectors comprising expression regulatory elements operably linked to any of the nucleic acid sequences included within the scope of the present invention.

Methods are also provided herein for producing FGF-21. Preparation can be by isolation from conditioned medium from a variety of cell types so long as the cell type produces FGF-21. A second and preferred method involves utilization of recombinant methods by isolating or obtaining a nucleic acid sequence encoding FGF-21, cloning the sequence along with appropriate regulatory sequences into suitable vectors and cell types, and expressing the sequence to produce FGF-21.

Although FGF-21 has been described on the basis of its high expression level in liver, this factor may act on other cell types as well. It is likely that FGF-21 will act on non-liver cells to promote their survival, growth, differentiation state or function. This expectation is based upon the activity of known growth factors. Members of the FGF family act on many cell types of different function and embryologic origin, even when their expression is limited to one or a few tissues.

The inventors herein have identified that FGF-21 is expressed at a higher level in liver. This suggests a role for FGF-21 in, for example, precancerous lesions, hepatoma, cirrhosis, repair, from inflammatory diseases, trauma or other types of injury, and other diseases of the liver. Further, FGF-21 is also expressed in thymus and testis. This suggests a role for FGF-21 in, for example, infertility, control of testosterone production, cancer of the testis or associated cells, and other disorders of the testis, and in disorders of cells such as immune cells derived from the thymus, for example, autoimmune disorders, leukemias and lymphomas, immune deficiency states, and the like.

The present invention also includes therapeutic or pharmaceutical compositions comprising FGF-21 in an effective amount for treating patients with liver, testis or thymic disease, and a method comprising administering a therapeutically effective amount of FGF-21. These compositions and methods are useful for treating a number of diseases. The compositions and methods herein can also be useful to prevent degeneration and/or promote survival in other non-liver tissues as well, such as promoting angiogenesis, neuronal survival, wound healing, and the like. One skilled in the art can readily use a variety of assays known in the art to determine whether FGF-21 would be useful in promoting survival or functioning in a particular cell type. Promotion of neuronal survival is useful in the treatment of nervous system diseases and conditions, including Parkinson's disease, Alzheimers disease, traumatic injury to nerves, and degenerative disease of the nervous system.

In certain circumstances, it may be desirable to modulate or decrease the amount of FGF-21 expressed. Thus, in another aspect of the present invention, FGF-21 anti-sense oligonucleotides can be made and a method utilized for diminishing the level of expression of FGF-21 by a cell comprising administering one or more FGF-21 anti-sense oligonucleotides. By FGF-21 anti-sense oligonucleotides reference is made to oligonucleotides that have a nucleotide sequence that interacts through base pairing with a specific complementary nucleic acid sequence involved in the expression of FGF-21 such that the expression of FGF-21 is reduced. Preferably, the specific nucleic acid sequence involved in the expression of FGF-21 is a genomic DNA molecule or mRNA molecule that encodes FGF-21. This genomic DNA molecule can comprise regulatory regions of the FGF-21 gene, or the coding sequence for mature FGF-21 protein. The term complementary to a nucleotide sequence in the context of FGF-21 antisense oligonucleotides and methods therefor means sufficiently complementary to such a sequence as to allow hybridization to that sequence in a cell, i.e., under physiological conditions. The FGF-21 antisense oligonucleotides preferably comprise a sequence containing from about 8 to about 100 nucleotides and more preferably the FGF-21 antisense oligonucleotides comprise from about 15 to about 30 nucleotides. The FGF-21 antisense oligonucleotides can also contain a variety of modifications that confer resistance to nucleolytic degradation such as, for example, modified internucleoside linages (Uhlmann and Peyman, *Chemical Reviews* 90:543–548 1990; Schneider and Banner, *Tetrahedron Lett.* 31:335, 1990 which are incorporated by reference), modified nucleic acid bases and/or sugars and the like.

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation.

FGF-21 can also be linked or conjugated with agents that provide desirable pharmaceutical or pharmacodynamic properties. For example, FGF-21 can be coupled to any substance known in the art to promote penetration or transport across the blood-brain barrier such as an antibody to the transferring receptor, and administered by intravenous injection (see, for example, Friden et al., *Science* 259:373–377, 1993 which is incorporated by reference). Furthermore, FGF-21 can be stably linked to a polymer such as polyethylene glycol to obtain desirable properties of solubility, stability, half-life and other pharmaceutically advantageous properties. (See, for example, Davis et al., *Enzyme Eng.* 4:169–73, 1978; Burnham, *Am. J. Hosp. Pharm.* 51:210–218, 1994 which are incorporated by reference.)

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. FGF-21 can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing FGF-21 are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

Depending on the treatment regimen contemplated, it may be desired to control the rate of release of FGF-21 protein or variant thereof to provide long-term treatment while minimizing the frequency of administration. Such treatment regimens may be desired, for example, where the FGF-21 protein is found to be relatively unstable such that the localized concentration of active protein is at an efficacious level for an insufficient period of time. Thus, for example, for certain diseases, it may not be desired or practical to perform repeated and frequent injections. The major advantages of such sustained release systems include targeted local delivery of drugs at a constant rate, less drug required to treat the disease state, minimization of possible side effects, and enhanced efficacy of treatment. Also, these forms of delivery systems are capable of protecting drugs that are unstable in vivo and that would normally require a frequent dosing interval. Under such circumstances, sustained release may be achieved by one of the methods readily available in the art such as the encapsulation of FGF-21 conjugated heparin-Sepharose beads to form heparin-alginate microspheres or the preparation of FGF-21 PLG microspheres.

Heparin-alginate microspheres have been successfully employed for the delivery of Basic Fibroblast Growth Factor to tissue (Lopez et al., *Journal of Pharmacology and Experimental Therapeutics* 282(1):385–390 (1997)). Similarly, Alginate/heparin-Sepharose microspheres and films have been used as drug carriers to control the release of a basic FGF-saponin conjugate in order to control its release in small doses. Addition of heparin to solutions of bFGF prevents losses in activity that accompany changes in pH or elevation in temperature. See, for example, Gospodarowicz et al., *J. Cell. Physiol.* 128:475–484 (1986).

Binding of FGF-21 to heparin may be employed in order to enhance its stability either during in vivo expression or administration or in vitro during various stages of protein purification. Thus, by the present invention, heparin may be added to a solution of FGF-21 and the activity assayed by the methods disclosed herein.

FGF-21 bound heparin-Sepharose beads may be encapsulated into calcium alginate microspheres to permit the controlled release of the heparin-stabilized FGF-21 protein. For example, microspheres may be constructed by dropping a mixed solution of sodium alginate with FGF-21 bound heparin-Sepharose beads into a hardening solution of calcium chloride. Spheres are formed instantaneously as the mixture enters the hardening solution. The size of the microsphere may be adjusted by passing the FGF-21 bound heparin-Sepharose beads through a cylinder of reduced cross-sectional area such as through a hypodermic needle.

Encapsulation efficiency may be determined by comparing the amount of encapsulated growth factor with that initially present in solution. For example, the FGF-21 may be stripped from the heparin-Sepharose beads with a solution of 3 M NaCl and functional activity assays may be performed.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, FGF-21 may be therapeutically administered by implanting into patients vectors or cells capable of producing a biologically-active form of FGF-21 or a precursor of FGF-21, i.e., a molecule that can be readily converted to a biological-active form of FGF-21 by the body. In one approach cells that secrete FGF-21 may be encapsulated into semipermeable membranes for implantation into a patient. The cells can be cells that normally express FGF-21 or a precursor thereof or the cells can be transformed to express FGF-21 or a precursor thereof. It is preferred that the cell be of human origin and that the FGF-21 be human FGF-21 when the patient is human. However, the formulations and methods herein can be used for veterinary as well as human applications and the term "patient" as used herein is intended to include human and veterinary patients.

Cells can be grown ex vivo for use in transplantation or engraftment into patients (Muench et al., *Leuk. & Lymph.* 16:1–11, 1994 which is incorporated by reference). In another embodiment of the present invention, FGF-21 is used to promote the ex vivo expansion of a cells for transplantation or engraftment. Current methods have used bioreactor culture systems containing factors such as erythropoietin, colony stimulating factors, stem cell factor, and interleukins to expand hematopoietic progenitor cells for erythrocytes, monocytes, neutrophils, and lymphocytes (Verfaillie, *Stem Cells* 12:466–476, 1994 which is incorporated by reference). These stem cells can be isolated from the marrow of human donors, from human peripheral blood, or from umbilical cord blood cells. The expanded blood cells are used to treat patients who lack these cells as a result of specific disease conditions or as a result of high dose chemotherapy for treatment of malignancy (George, *Stem Cells* 12(Suppl 1):249–255, 1994 which is incorporated by reference). In the case of cell transplant after chemotherapy, autologous transplants can be performed by removing bone marrow cells before chemotherapy, expanding the cells ex vivo using methods that also function to purge malignant cells, and transplanting the expanded cells back into the patient following chemotherapy (for review, see Rummel and Van Zant, *J. Hematotherapy* 3:213–218, 1994 which is incorporated by reference). Since FGF-21 is expressed in liver cells, it is believed that FGF-21 can function to prevent or slow the progression of cirrhosis changes in liver cells, and to promote hepatic cell regeneration after injury or after surgical removal of part of the liver due to disease.

In a number of circumstances it would be desirable to determine the levels of FGF-21 in a patient. The identification of FGF-21 along with the present report showing expression of FGF-21 provides the basis for the conclusion that the presence of FGF-21 serves a normal physiological function related to cell growth and survival. Endogenously produced FGF-21 may also play a role in certain disease conditions.

Given that FGF-21 is expressed in liver, thymic and testicular tissue, it is likely that the level of FGF-21 may be altered in a variety of conditions and that quantification of FGF-21 levels would provide clinically useful information. Furthermore, in the treatment of degenerative conditions, altered physiological function or in recovery from injury to the liver, testis or thymic cells, compositions containing FGF-21 can be administered and it would likely be desirable to achieve certain target levels of FGF-21 in sera or in any desired tissue compartment. It would, therefore, be advantageous to be able to monitor the levels of FGF-21 in a patient. Accordingly, the present invention also provides methods for detecting the presence of FGF-21 in a sample from a patient.

The term "detection" as used herein in the context of detecting the presence of FGF-21 in a patient is intended to include determining the amount of FGF-21 or the ability to express an amount of FGF-21 in a patient, distinguishing FGF-21 from other growth factors, the estimation of prognosis in terms of probable outcome of a degenerative disease and prospect for recovery, monitoring the FGF-21 levels over a period of time as a measure of status of the condition, and monitoring FGF-21 levels for determining a preferred therapeutic regimen for the patient.

To detect the presence of FGF-21 in a patient, a sample is obtained from the patient. The sample can be a tissue biopsy sample or a sample of blood, plasma, serum, CSF or the like. FGF-21 is expressed in liver tissues, as discussed in Example 2. Samples for detecting FGF-21 can be taken from this tissue. When assessing the levels of FGF-21 in the liver, thymus or testis, a preferred sample is a sample taken from these tissues or from veins draining these tissues.

In some instances it is desirable to determine whether the FGF-21 gene is intact in the patient or in a tissue or cell line within the patient. By an intact FGF-21 gene it is meant that there are no alterations in the gene such as point mutations, deletions, insertions, chromosomal breakage, chromosomal rearrangements and the like wherein such alteration might alter production of FGF-21 or alter its biological activity, stability or the like to lead to disease processes or susceptibility to cellular degenerative conditions. Thus, in one embodiment of the present invention a method is provided for detecting and characterizing any alterations in the FGF-21 gene. The method comprises providing an oligonucleotide that contains the FGF-21 cDNA, genomic DNA or a fragment thereof or a derivative thereof. By a derivative of an oligonucleotide, it is meant that the derived oligonucleotide is substantially the same as the sequence from which it is derived in that the derived sequence has sufficient sequence complementarily to the sequence from which it is derived to hybridize to the FGF-21 gene. The derived nucleotide sequence is not necessarily physically derived from the nucleotide sequence, but may be generated in any manner including for example, chemical synthesis or DNA replication or reverse transcription or transcription.

Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact FGF-21 gene or an FGF-21 gene abnormality.

Hybridization to an FGF-21 gene would involve denaturing the chromosomal DNA to obtain a single-stranded DNA; contacting the single-stranded DNA with a gene probe associated with the FGF-21 gene sequence; and identifying the hybridized DNA-probe to detect chromosomal DNA containing at least a portion of a human FGF-21 gene.

The term "probe" as used herein refers to a structure comprised of a polynucleotide that forms a hybrid structure with a target sequence, due to complementarity of probe sequence with a sequence in the target region. Oligomers suitable for use as probes may contain a minimum of about 8–12 contiguous nucleotides which are complementary to the targeted sequence and preferably a minimum of about 20.

The FGF-21 gene probes of the present invention can be DNA or RNA oligonucleotides and can be made by any method known in the art such as, for example, excision, transcription or chemical synthesis. Probes may be labeled with any detectable label known in the art such as, for example, radioactive or fluorescent labels or enzymatic marker. Labeling of the probe can be accomplished by any method known in the art such as by PCR, random priming, end labeling, nick translation or the like. One skilled in the art will also recognize that other methods not employing a labeled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25°–45° C., more preferably at 32°–40° C. and more preferably at 37°–38° C. The time required for hybridization is from about 0.25 to about 96 hours, more preferably from about one to about 72 hours, and most preferably from about 4 to about 24 hours.

FGF-21 gene abnormalities can also be detected by using the PCR method and primers that flank or lie within the FGF-21 gene. The PCR method is well known in the art. Briefly, this method is performed using two oligonucleotide primers which are capable of hybridizing to the nucleic acid sequences flanking a target sequence that lies within an FGF-21 gene and amplifying the target sequence. The terms "oligonucleotide primer" as used herein refers to a short strand of DNA or RNA ranging in length from about 8 to about 30 bases. The upstream and downstream primers are typically from about 20 to about 30 base pairs in length and hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, the method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize with the strand being amplified.

After PCR amplification, the DNA sequence comprising FGF-21 or pre-pro FGF-21 or a fragment thereof is then directly sequenced and analyzed by comparison of the sequence with the sequences disclosed herein to identify alterations which might change activity or expression levels or the like.

In another embodiment, a method for detecting FGF-21 is provided based upon an analysis of tissue expressing the FGF-21 gene. Certain tissues such as those identified below in Example 2 have been found to express the FGF-21 gene. The method comprises hybridizing a polynucleotide to mRNA from a sample of tissues that normally express the FGF-21 gene. The sample is obtained from a patient suspected of having an abnormality in the FGF-21 gene or in the FGF-21 gene of particular cells.

To detect the presence of mRNA encoding FGF-21 protein, a sample is obtained from a patient. The sample can be from blood or from a tissue biopsy sample. The sample may be treated to extract the nucleic acids contained therein. The resulting nucleic acid from the sample is subjected to gel electrophoresis or other size separation techniques.

The mRNA of the sample is contacted with a DNA sequence serving as a probe to form hybrid duplexes. The use of a labeled probes as discussed above allows detection of the resulting duplex.

When using the cDNA encoding FGF-21 protein or a derivative of the cDNA as a probe, high stringency conditions can be used in order to prevent false positives, that is the hybridization and apparent detection of FGF-21 nucleotide sequences when in fact an intact and functioning FGF-21 gene is not present. When using sequences derived from the FGF-21 cDNA, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al., Molecular Cloning: A Laboratory Manual, $2^{nd}$ Ed. (1989) Cold Spring Harbor Press, Cold Spring Harbor, N.Y.

In order to increase the sensitivity of the detection in a sample of mRNA encoding the FGF-21 protein, the technique of reverse transcription/polymerization chain reaction (RT/PCR) can be used to amplify cDNA transcribed from mRNA encoding the FGF-21 protein. The method of RT/PCR is well known in the art, and can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and FGF-21 specific primers. (Belyavsky et al., *Nucl. Acid Res.* 17:2919–2932, 1989; Krug and Berger, *Methods in Enzymology*, 152:316–325, Academic Press, NY, 1987 which are incorporated by reference).

The polymerase chain reaction method is performed as described above using two oligonucleotide primers that are substantially complementary to the two flanking regions of the DNA segment to be amplified.

Following amplification, the PCR product is then electrophoresed and detected by ethidium bromide staining or by phosphoimaging.

The present invention further provides for methods to detect the presence of the FGF-21 protein in a sample obtained from a patient. Any method known in the art for detecting proteins can be used. Such methods include, but are not limited to immunodiffusion, immunoelectrophoresis, immunochemical methods, binder-ligand assays, immuno-histochemical techniques, agglutination and complement assays. (for example, see *Basic and Clinical Immunology*, 217–262, Sites and Terr, eds., Appleton & Lange, Norwalk, Conn., 1991 which is incorporated by reference). Preferred are binder-ligand immunoassay methods including reacting antibodies with an epitope or epitopes of the FGF-21 protein and competitively displacing a labeled FGF-21 protein or derivative thereof. Preferred antibodies are prepared according to Example 4.

As used herein, a derivative of the FGF-21 protein is intended to include a polypeptide in which certain amino acids have been deleted or replaced or changed to modified or unusual amino acids wherein the FGF-21 derivative is biologically equivalent to FGF-21 and wherein the polypeptide derivative cross-reacts with antibodies raised against the FGF-21 protein. By cross-reaction it is meant that an antibody reacts with an antigen other than the one that induced its formation.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Polyclonal or monoclonal antibodies to the FGF-21 protein or an epitope thereof can be made for use in immunoassays by any of a number of methods known in the art. By epitope reference is made to an antigenic determinant of a polypeptide. An epitope could comprise 3 amino acids in a spatial conformation which is unique to the epitope. Generally an epitope consists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse (see Example 4).

Oligopeptides can be selected as candidates for the production of an antibody to the FGF-21 protein based upon the oligopeptides lying in hydrophilic regions, which are thus likely to be exposed in the mature protein. Preferred oligopeptides are RQRYLYTDDAQQTEAH (residues 46–61 of SEQ NO:4) and HLPGNKSPHRDPAPR (residues 146–160 of SEQ ID NO:4). Additional oligopeptides can be determined using, for example, the Antigenicity Index of Welling, G.W. et al., *FEBS Lett.* 188:215–218, 1985, incorporated herein by reference.

Antibodies to FGF-21 can also be raised against oligopeptides that include one or more of the conserved regions identified herein such that the antibody can cross-react with other family members. Such antibodies can be used to identify and isolate the other family members.

Methods for preparation of the FGF-21 protein or an epitope thereof include, but are not limited to chemical synthesis, recombinant DNA techniques or isolation from biological samples. Chemical synthesis of a peptide can be performed, for example, by the classical Merrifield method of solid phase peptide synthesis (Merrifield, *J. Am. Chem. Soc.* 85:2149, 1963 which is incorporated by reference) or the FMOC strategy on a Rapid Automated Multiple Peptide Synthesis system (E. I. du Pont de Nemours Company, Wilmington, Del.) (Caprino and Han, *J. Org. Chem.* 37:3404, 1972 which is incorporated by reference).

Polyclonal antibodies can be prepared by immunizing rabbits or other animals by injecting antigen followed by subsequent boosts at appropriate intervals. The animals are bled and sera assayed against purified FGF-21 protein usually by ELISA or by bioassay based upon the ability to block the action of FGF-21 on liver or other cells. When using avian species, e.g., chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. (Milstein and Kohler, *Nature* 256:495–497, 1975; Gulfre and Milstein, *Methods in Enzymology: Immunochemical Techniques* 73:1–46, Langone and Banatis eds., Academic Press, 1981 which are incorporated by reference). The hybridoma cells so formed are then cloned by limiting dilution methods and supernates assayed for antibody production by ELISA, RIA or bioassay.

The unique ability of antibodies to recognize and specifically bind to target proteins provides an approach for treating an overexpression of the protein. Thus, another aspect of the present invention provides for a method for preventing or treating diseases involving overexpression of the FGF-21 protein by treatment of a patient with specific antibodies to the FGF-21 protein.

Specific antibodies, either polyclonal or monoclonal, to the FGF-21 protein can be produced by any suitable method known in the art as discussed above. For example, murine or human monoclonal antibodies can be produced by hybridoma technology or, alternatively, the FGF-21 protein, or an immunologically active fragment thereof, or an anti-idiotypic antibody, or fragment thereof can be administered to an animal to elicit the production of antibodies capable of recognizing and binding to the FGF-21 protein. Such antibodies can be from any class of antibodies including, but not limited to IgG, IgA, IgM, IgD, and IgE or in the case of avian species, IgY and from any subclass of antibodies.

Polypeptides encoded by the instant polynucleotides and corresponding full-length genes can be used to screen peptide libraries, protein libraries, small molecule libraries, and phage display libraries, and other known methods, to identify analogs or antagonists.

Native FGF polypeptides may play a role in cancer. For example, FGF family members can induce marked morphological transformation of NIH 3T3 cells, and exhibit strong tumorigenicity in nude mice. Angiogenic activity has been exhibited by FGF family members. Thus, inhibitors of FGF can be used to treat cancer, such as prostate cancer.

A library of peptides may be synthesized following the methods disclosed in U.S. Pat. No. 5,010,175, and in PCT No. WO 91/17823. As described below in brief, a mixture of peptides is prepared, which is then screened to identify the peptides exhibiting the desired signal transduction and receptor binding activity. According to the method of the '175 patent, a suitable peptide synthesis support (e.g., a resin) is coupled to a mixture of appropriately protected, activated amino acids. The concentration of each amino acid in the reaction mixture is balanced or adjusted in inverse proportion to its coupling reaction rate so that the product is an equimolar mixture of amino acids coupled to the starting resin. The bound amino acids are then deprotected, and reacted with another balanced amino acid mixture to form an equimolar mixture of all possible dipeptides. This process is repeated until a mixture of peptides of the desired length (e.g., hexamers) is formed. Note that one need not include all amino acids in each step: one may include only one or two amino acids in some steps (e.g., where it is known that a particular amino acid is essential in a given position), thus reducing the complexity of the mixture. After the synthesis of the peptide library is completed, the mixture of peptides is screened for binding to the selected polypeptide. The peptides are then tested for their ability to inhibit or enhance activity. Peptides exhibiting the desired activity are then isolated and sequenced.

The method described in PCT No. WO 91/17823 is similar. However, instead of reacting the synthesis resin with a mixture of activated amino acids, the resin is divided into twenty equal portions (or into a number of portions corresponding to the number of different amino acids to be added in that step), and each amino acid is coupled individually to its portion of resin. The resin portions are then combined, mixed, and again divided into a number of equal portions for reaction with the second amino acid. In this manner, each reaction may be easily driven to completion. Additionally, one may maintain separate "subpools" by treating portions in parallel, rather than combining all resins at each step. This simplifies the process of determining which peptides are responsible for any observed receptor binding or signal transduction activity.

In such cases, the subpools containing, e.g., 1–2,000 candidates each are exposed to one or more polypeptides of the invention. Each subpool that produces a positive result is then resynthesized as a group of smaller subpools (subsubpools) containing, e.g., 20–100 candidates, and reassayed. Positive sub-subpools may be resynthesized as individual compounds, and assayed finally to determine the peptides that exhibit a high binding constant. These peptides can be tested for their ability to inhibit or enhance the native activity. The methods described in PCT No. WO 91/7823 and U.S. Pat. No. 5,194,392 (herein incorporated by reference) enable the preparation of such pools and subpools by automated techniques in parallel, such that all synthesis and resynthesis may be performed in a matter of days.

Peptide agonists or antagonists are screened using any available method, such as signal transduction, antibody binding, receptor binding and mitogenic assays. The assay conditions ideally should resemble the conditions under which the native activity is exhibited in vivo, that is, under physiologic pH, temperature, and ionic strength. Suitable agonists or antagonists will exhibit strong inhibition or enhancement of the native activity at concentrations that do not cause toxic side effects in the subject. Agonists or antagonists that compete for binding to the native polypeptide may require concentrations equal to or greater than the native concentration, while inhibitors capable of binding irreversibly to the polypeptide may be added in concentrations on the order of the native concentration.

The availability of hFGF-21 and mFGF-21 allows for the identification of small molecules and low molecular weight compounds that inhibit the binding of FGF-21 to its receptor, through routine application of high-throughput screening methods (HTS). HTS methods generally refer to technologies that permit the rapid assaying of lead compounds for therapeutic potential. HTS techniques employ robotic handling of test materials, detection of positive signals, and interpretation of data. Lead compounds may be identified via the incorporation of radioactivity or through optical assays that rely on absorbance, fluorescence or luminescence as read-outs. Gonzalez, J. E. et al., (1998) *Curr. Opin. Biotech.* 9:624–631. Assays for detecting interaction between an FGF molecule and FGF receptor are described in, for example, Blunt, A. G. et al., (1997) *J. Biol. Chem.* 272:3733–3738, and such assays can be adapted for determining if a candidate molecule can inhibit the interaction between FGF-21 and its receptor.

Model systems are available that can be adapted for use in high throughput screening for compounds that inhibit the interaction of FGF-21 with its receptor, for example by competing with FGF-21 for receptor binding. Sarubbi et al., (1996) *Anal. Biochem.* 237:70–75 describe cell-free, non-isotopic assays for identifying molecules that compete with natural ligands for binding to the active site of IL-1 receptor. Martens, C. et al., (1999) *Anal. Biochem.* 273:20–31 describe a generic particle-based nonradioactive method in which a labeled ligand binds to its receptor immobilized on a particle; label on the particle decreases in the presence of a molecule that competes with the labeled ligand for receptor binding.

The therapeutic FGF-21 polynucleotides and polypeptides of the present invention may be utilized in gene delivery vehicles. The gene delivery vehicle may be of viral or non-viral origin (see generally, Jolly, *Cancer Gene Therapy* 1:51–64 (1994); Kimura, *Human Gene Therapy* 5:845–852 (1994); Connelly, *Human Gene Therapy* 1:185–193 (1995); and Kaplitt, *Nature Genetics* 6:148–153 (1994)). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 731; WO 90/07936; WO 94/03622; WO 93/25698; WO 93/25234; U.S. Pat. No. 5,219,740; WO 93/11230; WO 93/10218; Vile and Hart, *Cancer Res.* 53:3860–3864 (1993); Vile and Hart, *Cancer Res.* 53:962–967 (1993); Ram et al., *Cancer Res.* 53:83–88 (1993); Takamiya et al., *J. Neurosci. Res.* 33:493–503 (1992); Baba et al., *J. Neurosurg.* 79:729–735 (1993); U.S. Pat. No. 4,777,127; GB Pat. No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., *J. Vir.* 63:3822–3828 (1989); Mendelson et al., *Virol.* 166: 154–165 (1988); and Flotte et al., *P.N.A.S.* 90:10613–10617 (1993).

Representative examples of adenoviral vectors include those described by Berkner, *Biotechniques* 6:616–627 (Biotechniques); Rosenfeld et al., *Science* 252:431–434 (1991); WO 93/19191; Kolls et al., *P.N.A.S.* :215–219 (1994); Kass-Eisler et al., *P.N.A.S.* 90:11498–11502 (1993); Guzman et al., *Circulation* 88:2838–2848 (1993); Guzman et al., *Cir. Res.* 73:1202–1207 (1993); Zabner et al., *Cell* 75:207–216 (1993); Li et al., *Hum. Gene Ther.* 4:403–409 (1993); Cailaud et al., *Eur. J. Neurosci.* 5:1287–1291 (1993); Vincent et al., *Nat. Genet.* 5:130–134 (1993); Jaffe et al., *Nat. Genet.* 1:372–378 (1992); and Levrero et al., *Gene* 101:195–202 (1992). Exemplary adenoviral gene therapy vectors employable in this invention also include those described in WO 94/12649, WO 93/03769; WO 93/19191; WO 94/28938; WO95/11984 and WO 95/00655. Administration of DNA linked to killed adenovirus as described in Curiel, *Hum. Gene Ther.* 3:147–154 (1992) may be employed.

Other gene delivery vehicles and methods may be employed, including polycationic condensed DNA linked or unlinked to killed adenovirus alone, for example Curiel, *Hum. Gene Ther.* 3:147–154 (1992); ligand-linked DNA, for example see Wu, *J. Biol. Chem.* 264:16985–16987 (1989); eukaryotic cell delivery vehicles cells, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol. Cell Biol.* 14:2411–2418 (1994), and in Woffendin, *Proc. Natl. Acad Sci.* 91:1581–1585 (1994).

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422, 120, PCT patent publication Nos. WO 95/13796, WO 94/23697, and WO 91/14445, and EP No. 0 524 968.

Further non-viral delivery suitable for use includes mechanical delivery systems such as the approach described in Woffendin et al., *Proc. Natl. Acad. Sci. USA* 91(24): 11581–11585 (1994). Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT patent publication No. WO 92/11033.

FGF has been implicated in diseases characterized by loss of function, inadequate function/number, abnormal function or death of cells, tissues or organs for which function or survival can be prolonged/rescued, and abnormalities reversed or prevented by therapy with FGF.

Loss of pulmonary, bronchia or alveolar cells or function, healing of pulmonary or bronchia wounds, pulmonary infraction, emphysema/chronic obstructive pulmonary disease, asthma, sequelae of infectious or autoimmune disease, sequelae of pulmonary arterial or venous hypertension, pulmonary fibrosis, pulmonary disease of immaturity, and cystic fibrosis are conditions amenable to treatment with FGF.

Ischemic vascular disease may be amenable to FGF-21 treatment, wherein the disease is characterized by inadequate blood flow to an organ(s). Treatment may induce therapeutic angiogenesis or preserve function/survival of cells (myocardial ischemia/infarction, peripheral vascular disease, renal artery disease, stroke). Cardiomyopathies characterized by loss of function or death of cardiac myocytes or supporting cells in the heart (congestive heart failure, myocarditis) may also be treated using FGF-21, as can musculoskeletal disease characterized by loss of function, inadequate function or death of skeletal muscle cells, bone cells or supporting cells. Examples include skeletal myopathies, bone disease, and arthritis.

FGF-21 polynucleotides and polypeptides may aid in correction of congenital defects due to loss of FGF-21 molecule or its function (liver, heart, lung, brain, limbs, kidney, etc.).

Treatment of wound healing is yet another use of FGF-21 polypeptides and polynucleotides, either due to trauma, disease, medical or surgical treatment, including regeneration of cell populations and tissues depleted by these processes. Examples include liver regeneration, operative wound healing, re-endothelialization of injured blood vessels, healing of traumatic wounds, healing of ulcers due to vascular, metabolic disease, etc., bone fractures, loss of cells due to inflammatory disease, etc.

FGF-21 may also be used in screens to identify drugs for treatment of cancers which involve over activity of the molecule, or new targets which would be useful in the identification of new drugs.

For all of the preceding embodiments, the clinician will determine, based on the specific condition, whether FGF-21 polypeptides or polynucleotides, antibodies to FGF-21, or small molecules such as peptide analogues or antagonists, will be the most suitable form of treatment. These forms are all within the scope of the invention.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLES

Example 1

Isolation and Analysis of Mouse FGF-21—DNA was prepared from mouse embryo cDNA. DNA was amplified from mouse embryo cDNA by polymerase chain reaction (PCR) for 30 cycles in 25 μl of a reaction mixture containing each of the sense and antisense degenerate primers representing all possible codons corresponding to the amino acid sequences of human FGF-19, RPYDGYN and LPMLPM, respectively. The amplified product was further amplified by PCR with each of the sense and antisense degenerate primers representing all possible codons corresponding to the amino acid sequences of human FGF-19, RPDGYN and HFLPML, respectively. The amplified DNAs of expected size (approximately 120 base pairs) were cloned. By determination of the nucleotide sequences of the cloned DNAs, a novel mouse FGF, FGF-21, cDNA was identified. To determine the entire coding region of the novel FGF cDNA, the coding region was amplified from mouse embryo cDNA by adaptor-ligation mediated PCR using a Marathon cDNA amplification kit (Clontech, Palo Alto, Calif.) and primers specific for the FGF. The cDNA encoding the entire coding region of the FGF was amplified from mouse embryo cDNA by PCR using the FGF-specific primers including the 5' and 3' noncoding sequences, and cloned into the pGEM-T DNA vector. The nucleotide sequence is shown in SEQ ID NO:1 and the amino acid sequence is shown in SEQ ID NO:2.

Example 2

Expression of FGF-21 in Mouse Tissues—Poly (A)+ RNA (10 μg) from mouse tissues was dissolved on a denaturing agarose gel (1%) containing formaldehyde, and transferred to a nitrocellulose membrane in 20X SSC (1X SSC:0.15 M NAC1/0.015 M sodium citrate) overnight. A $^{32}$P-labeled FGF-21 cDNA probe (~650 base pairs) was labeled with a random primer labeling kit (Pharmacia Biotech, Uppsala, Sweden) and deoxycytidine 5'-[α-$^{32}$P-] triphosphate (~110 TBq/mmol) (ICN Biomedicals Inc., Costa Mesa, Calif.). The membrane was incubated in hybridization solution containing the labeled probe as described (Hoshikawa et al., *Biochem. Biophys. Res. Commun.* 244:187–191 (1998)), and analyzed with a radio-imaging analyzer (BAS 2000, Fuji Photo Film Co., Tokyo, Japan). As shown in FIG. 3, FGF-21 expression was most predominant in liver, with expression also seen in testis and thymus.

Example 3

Isolation and Analysis of Human FGF-21—The human FGF-21 gene was located in the 5' flanking region of a putative human alpha 1,2-fucosyltransferase gene. The cDNA encoding the entire coding region of human FGF-21 was amplified from fetal brain cDNA by PCR using the FGF-specific primers including the 5' and 3' noncoding sequences, and cloned into the pGEM-T DNA vector. The protein contains 209 amino acids, as shown in SEQ ID NO:4 (FIG. 5), and is encoded by the polynucleotide sequence of SEQ ID NO:3. Primers for amplification of human FGF-21 cDNA coding region are: sense primer for FGF-21: 5' agccattgatggactcggac 3'; antisense primer for FGF-21: 5' tggcttcaggaagcgtagct 3'.

Example 4

Preparation of Antisera to FGF-21 by Immunization of Rabbits with an FGF-21 Peptide—A peptide sequence corresponding to selected contiguous amino acids of the human FGF-21 protein is synthesized and coupled to keyhole limpet hemocyanin (KLH) as described (Harlow and Land, Antibodies: A Laboratory Manual, 1988. Cold Spring Harbor Laboratory, New York, N.Y.) The KLH-coupled peptide is used to immunize rabbits. Antisera are tested for specificity to FGF-21, and for cross-reactivity with other FGF proteins.

Exemplary peptide sequences are:

1. RQRYLYDDAQQTEAH (residues 46–61 of SEQ ID NO:4)

2. HLPGNKSPHRDPAPR
(residues 146–160 of SEQ ID NO:4)

All patents, published patent applications and publications cited herein are incorporated by reference as if set forth fully herein.

Although certain preferred embodiments have been described herein, it is not intended that such embodiments be construed as limitations on the scope of the invention except as set forth in the following claims.

We claim:

1. An epitope-bearing portion of the polypeptide of SEQ ID NO:4 for producing an antibody that binds to the polypeptide of SEQ ID NO: 4, wherein said epitope consists of the amino acid sequence of SEQ ID NO:8.

2. An isolated polypeptide comprising the amino acid sequence of SEQ ID NO: 4.

3. An isolated polypeptide consisting of the amino acid sequence of SEQ ID NO: 4.

* * * * *